(12) United States Patent
Han et al.

(10) Patent No.: US 10,112,922 B2
(45) Date of Patent: *Oct. 30, 2018

(54) INHIBITOR OF BRUTON'S TYROSINE KINASE

(71) Applicant: Centaurus BioPharma Co., Ltd., Haidian District, Beijing (CN)

(72) Inventors: Yongxin Han, Beijing (CN); Li Zhu, Beijing (CN); Dengming Xiao, Beijing (CN); Yong Peng, Beijing (CN); Hong Luo, Beijing (CN)

(73) Assignee: Centaurus BioPharma Co., Ltd., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/309,319

(22) PCT Filed: May 7, 2015

(86) PCT No.: PCT/CN2015/078453
§ 371 (c)(1),
(2) Date: Nov. 7, 2016

(87) PCT Pub. No.: WO2015/169233
PCT Pub. Date: Nov. 12, 2015

(65) Prior Publication Data
US 2017/0144986 A1  May 25, 2017

(30) Foreign Application Priority Data

May 7, 2014 (CN) .......................... 2014 1 0191608

(51) Int. Cl.
*C07D 401/04* (2006.01)
*C07D 231/38* (2006.01)
*C07D 403/04* (2006.01)

(52) U.S. Cl.
CPC ......... *C07D 401/04* (2013.01); *C07D 231/38* (2013.01); *C07D 403/04* (2013.01)

(58) Field of Classification Search
None
See application file for complete search history.

(56) References Cited

U.S. PATENT DOCUMENTS

2007/0298065 A1  12/2007  Jimenez et al.
2008/0108636 A1  5/2008  Honigberg et al.

FOREIGN PATENT DOCUMENTS

| CN | 101460466 A | 6/2009 |
| CN | 101610676 A | 12/2009 |
| CN | 103102349 A | 5/2013 |
| CN | 103848810 A | 6/2014 |
| JP | 2009-536617 A | 10/2009 |
| JP | 2010-504324 A | 2/2010 |
| WO | 2007/117692 A2 | 10/2007 |
| WO | 2008/039218 A2 | 4/2008 |
| WO | 2014/025976 A1 | 2/2014 |
| WO | 2014/068527 A1 | 5/2014 |
| WO | 2014/082598 A1 | 6/2014 |

OTHER PUBLICATIONS

International Search Report for corresponding International Application No. PCT/CN2015/078453 dated Jul. 13, 2015.
Office Action received in corresponding Chinese Application No. 201410191608.7 dated Jan. 18, 2017.
Extended European Search Report for corresponding European Application No. 15789528.5 dated Dec. 12, 2017.

*Primary Examiner* — Kamal A Saeed
(74) *Attorney, Agent, or Firm* — Renner, Otto, Boisselle & Sklar, LLP

(57) ABSTRACT

Provided are a compound represented by formula (III) or pharmaceutically acceptable salts, solvates, active metabolites, polymorphs, esters, tautomers or prodrugs thereof, pharmaceutical compositions containing the compound represented by formula (III), and the application of the pharmaceutical compositions as selective irreversible inhibitor of Bruton's tyrosine kinase for the prevention and treatment of inflammation, autoimmune diseases (such as rheumatoid arthritis) associated with aberrant B cell proliferation and cancers.

formula (III)

8 Claims, 1 Drawing Sheet

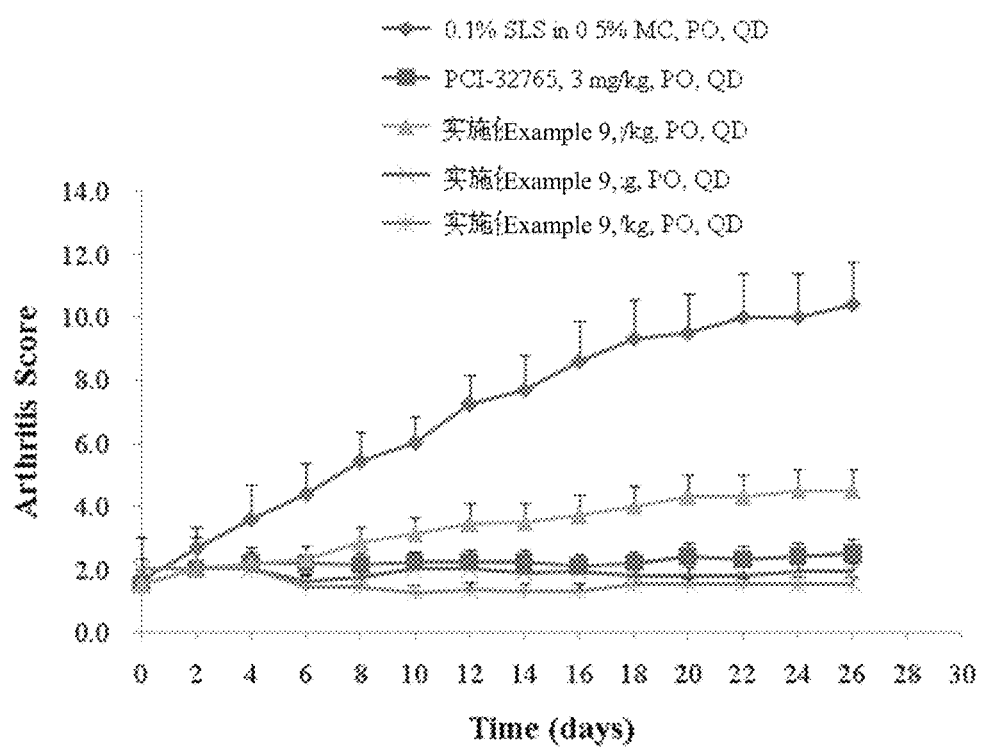

INHIBITOR OF BRUTON'S TYROSINE KINASE

This application is a national phase of International Application No. PCT/CN2015/078453 filed May 7, 2015, which claims priority to Application No. CN 201410191608.7 filed May 7, 2014.

FIELD OF THE INVENTION

This invention pertains to a series of multi-substituted five-membered heterocyclic compounds, which, as irreversible inhibitors of Bruton's tyrosine kinase, can be used alone or together with other therapeutic medicaments to treat inflammation, autoimmune diseases related to abnormal B-cell proliferation (such as rheumatoid arthritis) and cancer etc. This invention also pertains to pharmaceutical compositions comprising compounds of formula (III) and preparation methods thereof, use of the compounds in the preparation of medicaments and methods for preventing or treating mammals (especially human beings) suffering from diseases related to abnormal elevation of BTK kinase activity using the compounds of this invention.

BACKGROUND OF THE INVENTION

Protein kinases, the largest family of human enzymes, encompass well over 500 kinds of proteins. Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases.

Btk is a member of the Tec family of tyrosine kinases, and has been shown to be a critical regulator of early B-cell development and mature B-cell activation and survival (Khan et al. *Immunity* 1995 3:283; Ellmeier et al. *J. Exp. Med.* 2000 192:1611). B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause deregulated B-cell activation and/or the formation of pathogenic auto-antibodies leading to multiple autoimmune and/or inflammatory diseases.

Evidence for a role of Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl *Clin. Exp. Immunol.* 1993 94:459). A selective Btk inhibitor has been demonstrated dose-dependent efficacy in a mouse arthritis model (Pan et al., *Chem. Med Chem.* 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. *J Biol. Chem.* 2005 280:40261). This shows that Btk could be useful to treat pathological mast cell responses such as allergy and asthma. Also monocytes from XLA patients, in which Btk activity is absent, show decreased TNFα production following stimulation (Horwood et al. *J Exp Med* 197:1603, 2003). Therefore, TNFα mediated inflammation could be inhibited by small molecule inhibitors of Btk. Also, Btk has been reported to play a role in apoptosis (Islam and Smith *Immunol Rev* 178:49, 2000) and thus Btk inhibitors would be useful for the treatment of certain B-cell lymphomas and leukemia (Feldhahn et al. *J Exp Med* 201:1837, 2005).

On Jun. 16, 2012, Biopharmaceutical Company Pharmacyclics announced 2 new phase Ib/II clinical experimental results (PCYC-1102 and PCYC-1108) by using Btk inhibitor Ibrutinib (PCI-32765) for the treatment of chronic lymphocytic leukemia/small lymphocytic lymphoma (CLL/SLL). The experimental results showed high activity and good tolerance in 61 patients with relapsed/refractory and 31 untreated patients with CLL, and, during the test, none of the patients experienced drug withdrawal because of adverse events.

Obviously, the excellent clinical results of Ibrutinib show that highly selective small molecule Btk inhibitors will be another hot spot in the field of global drug development.

SUMMARY OF THE INVENTION

This invention provides a series of compounds of Formula (III), pharmaceutically acceptable salts, solvates, esters, acids and prodrugs thereof, compositions containing the compounds, and methods of treating diseases and disorders related to excessive BTK activities using the compounds.

In the first aspect the invention provides a compound of Formula (III), or a pharmaceutically acceptable salt, solvate, metabolite, polymorph, ester, tautomer or prodrug thereof,

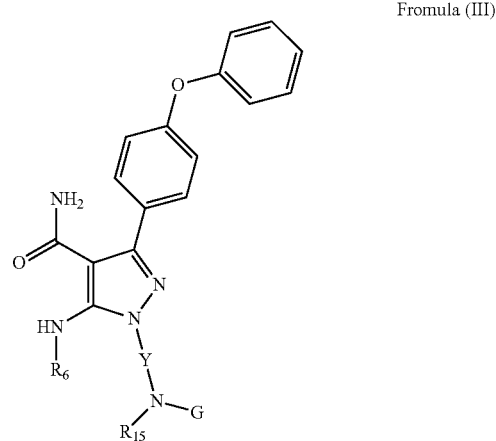

Fromula (III)

wherein:

Y is selected from the group consisting of substituted or unsubstituted alkyl and a 4-, 5- or 6-membered cycloalkyl ring; and $R_{15}$ is selected from the group consisting of H and lower alkyl; or, Y and $R_{15}$ may join to form a 4-, 5- or 6-membered heterocyclic ring; G is selected from the group consisting of H,

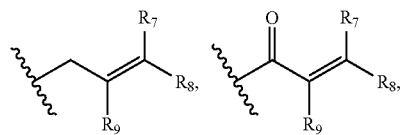

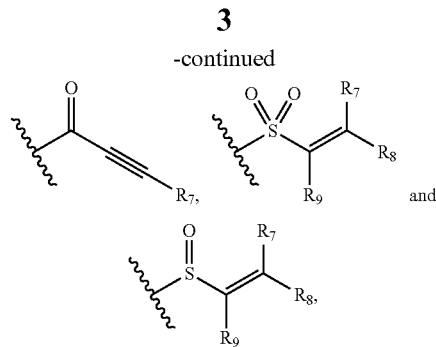

and

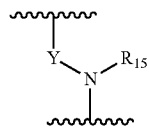

wherein R₇, R₈ and R₉ are each independently selected from the group consisting of H, halogen, —COOH, substituted or unsubstituted lower alkyl, and substituted or unsubstituted lower heteroalkyl;

R₆ is selected from the group consisting of H, —CH$_{1-8}$alkyl, —(CH$_2$)$_n$C$_{3-7}$cycloalkyl, —(CH$_2$)$_n$C$_{2-9}$heterocycloalkyl, —(CH$_2$)$_n$—OH, —(CH$_2$)$_n$—(CHOH)$_n$—H, —(CH$_2$)$_n$—O—(CH$_2$)$_n$CH$_3$, —(CH$_2$)$_n$—S—(CH$_2$)$_n$CH$_3$, —(CH$_2$)$_n$—NH$_2$, —(CH$_2$)$_n$—NH(C$_{1-8}$alkyl), —(CH$_2$)$_n$—N(C$_{1-8}$alkyl)$_2$ and —C(O)C$_{1-8}$alkyl;

n is 0, 1, 2, 3 or 4.

Preferably,

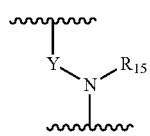

is selected from the group consisting of

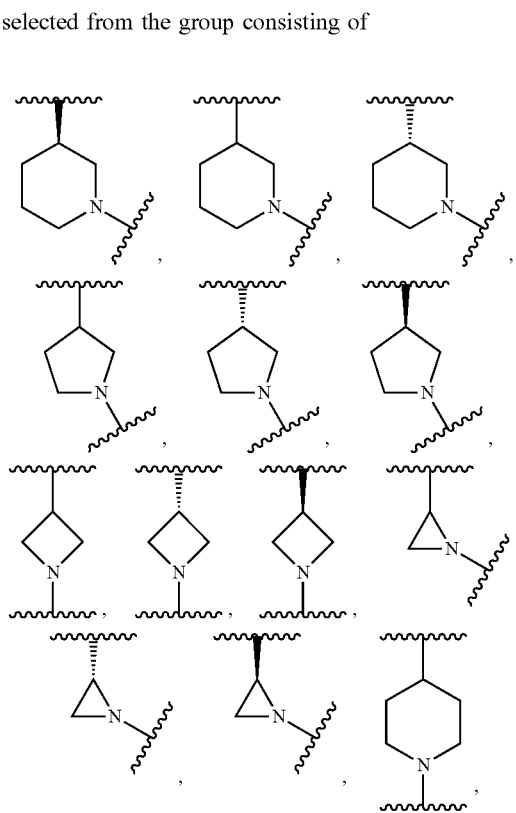

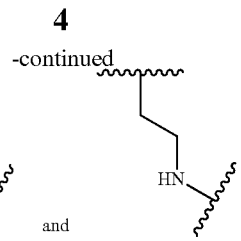

and

More preferably,

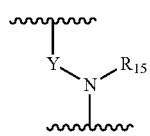

is selected from the group consisting of

[structures]

and

Even more preferably,

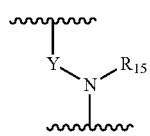

is selected from the group consisting of

[structures] and [structures].

Preferably, G is selected from the group consisting of

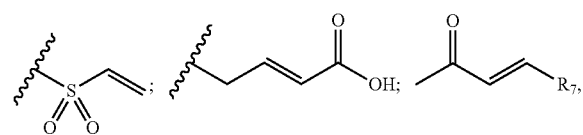

wherein R₇ is selected from the group consisting of H, —COOH and lower alkyl optionally substituted with the following groups: halogen, —OH, —O-lower alkyl, amino, monoalkylamino, dialkylamino, heterocycloalkylamino, alkylacyloxy and alkylsulfonamido; and

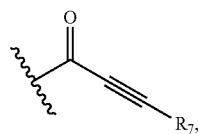

wherein R₇ is selected from H and lower alkyl.

More preferably, G is selected from the group consisting of

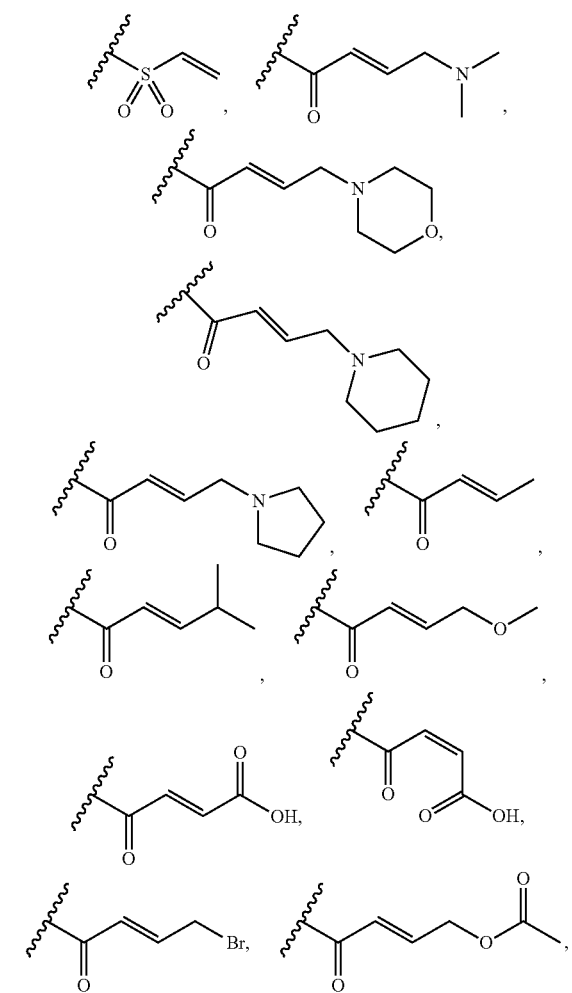

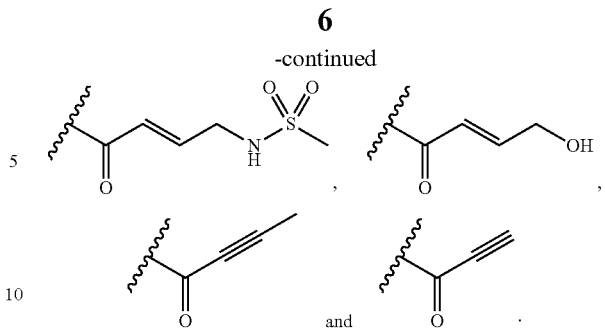

Preferably, R₆ is selected from the group consisting of H, Me, Et,

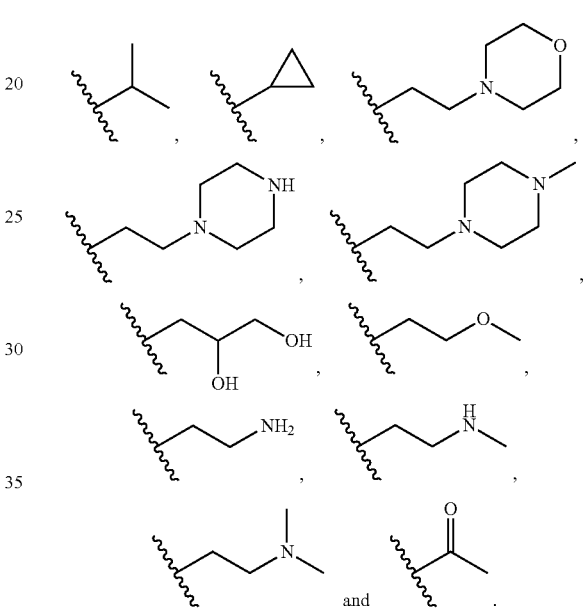

More preferably, R₆ is selected from the group consisting of H, Me and Et.

According to some embodiments, the compounds of this invention are those represented by any of the following formula:

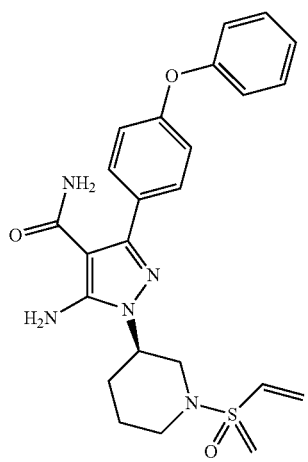

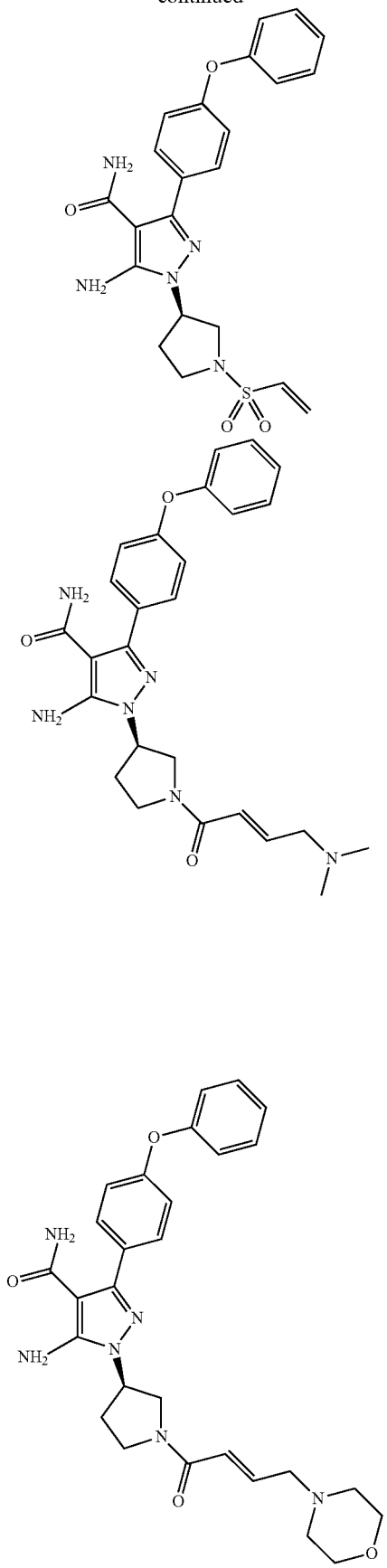
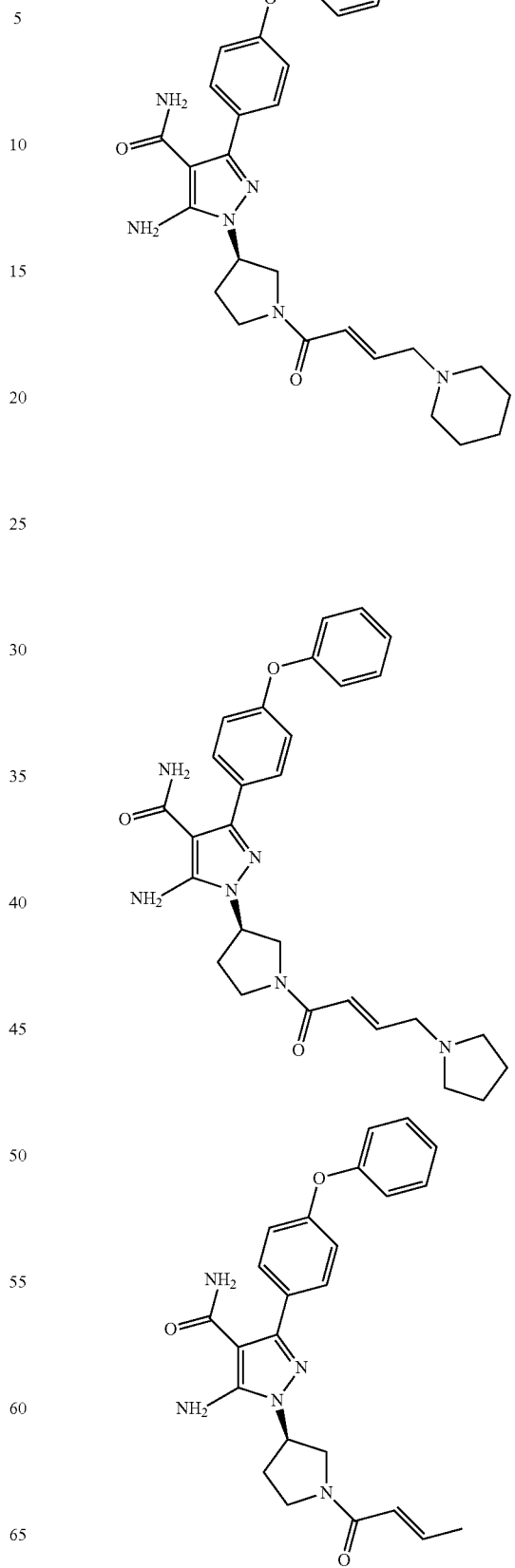

-continued
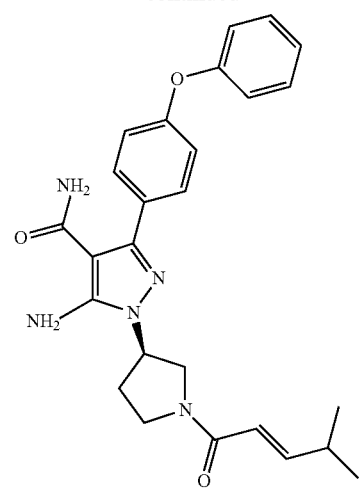
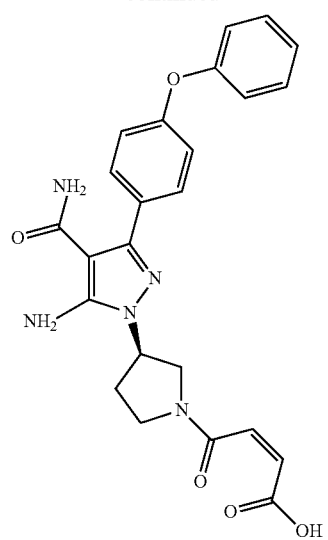
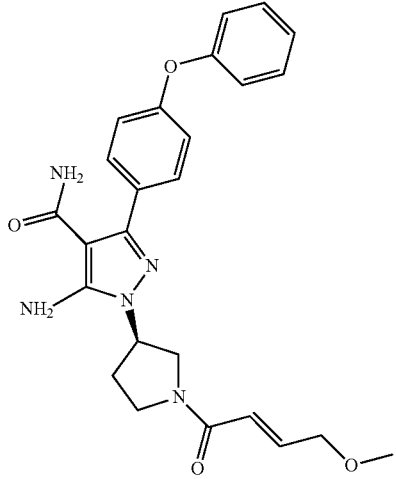
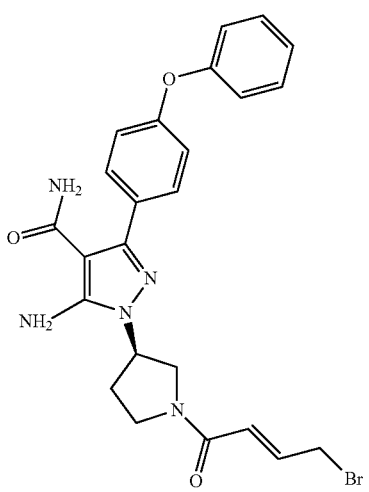
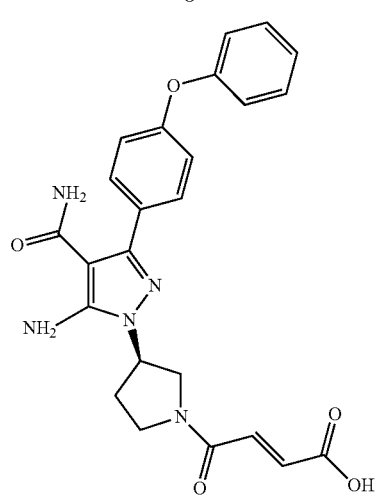
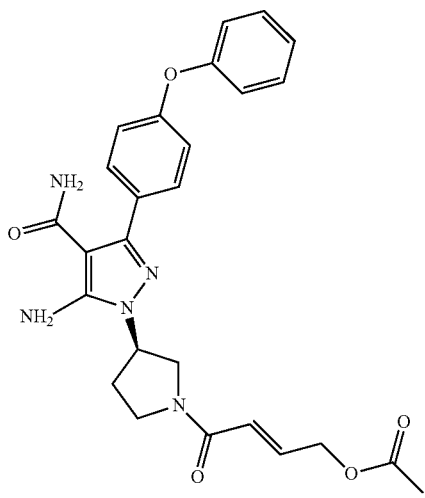

-continued

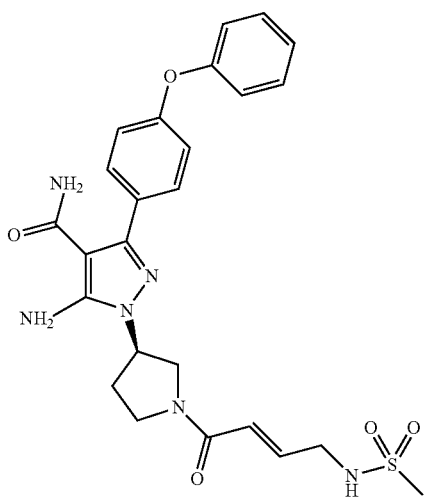

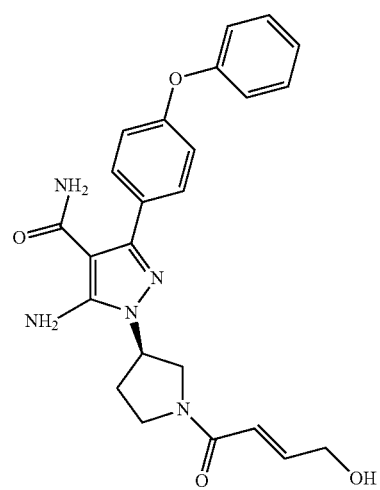

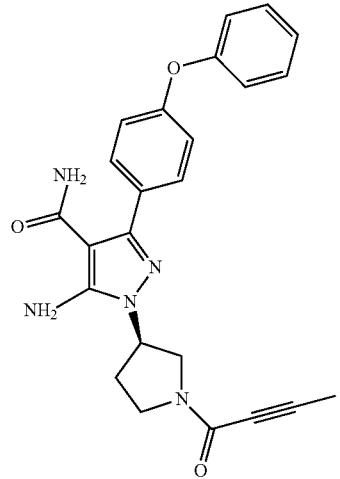

-continued

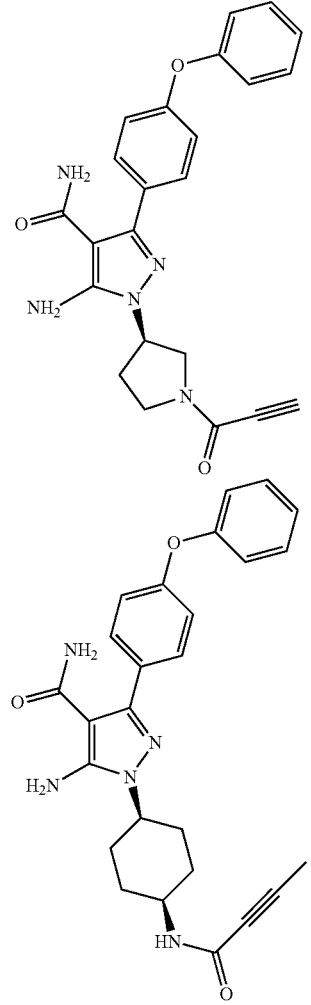

In the second aspect this invention pertains to use of a compound described above in the first aspect, or a pharmaceutically acceptable salt, solvate, metabolite, polymorph, ester, tautomer or prodrug thereof, as a medicament.

In the third aspect this invention pertains to a pharmaceutical composition comprising at least one compound described above in the first aspect, or a pharmaceutically acceptable salt, solvate, metabolite, polymorph, ester, tautomer or prodrug thereof, and any pharmaceutically accepted carrier.

In the fourth aspect this invention pertains to a method for treating heteroimmune diseases, inflammatory disease, asthma, arthritis, rheumatoid arthritis, systemic Lupus Erythematosus (SLE), or cancer such as B-cell histiocytosis, preferably chronic lymphocytic lymphoma, diffuse large B cell lymphoma, follicular lymphoma or chronic lymphocytic leukemia, comprising: administering to a mammal (especially a human being) in need thereof an therapeutically effective amount of a compound described above in the first aspect, or a pharmaceutically acceptable salt, solvate, metabolite, polymorph, ester, tautomer or prodrug thereof.

In the fifth aspect this invention pertains to a method for treating diseases related to abnormal elevation of BTK kinase activity of a mammal (especially a human being), comprising:

administering to the subject in need thereof an therapeutically effective amount of a compound described above in the first aspect, or a pharmaceutically acceptable salt, solvate, metabolite, polymorph, ester, tautomer or prodrug thereof.

In the sixth aspect this invention pertains to use of a compound described above in the first aspect, or a pharmaceutically acceptable salt, solvate, metabolite, polymorph, ester, tautomer or prodrug thereof, in the preparation of a medicament for treating or preventing a heteroimmune disease, inflammatory disease, asthma, arthritis, rheumatoid arthritis, systemic Lupus Erythematosus (SLE), or cancer such as B-cell histiocytosis, preferably chronic lymphocyte lymphoma, diffuse large B cell lymphoma, follicular lymphoma or chronic lymphocytic leukemia.

In the seventh aspect this invention pertains to use of a compound described above in the first aspect, or a pharmaceutically acceptable salt, solvate, metabolite, polymorph, ester, tautomer or prodrug thereof, in the preparation of a medicament for preventing or treating a mammal (especially a human being) suffering from diseases related to abnormal elevation of BTK kinase activity.

In the eighth aspect this invention pertains to a method to inhibit the BTK kinase activity, comprising: contacting the BTK kinase with a compound described above in the first aspect, or a pharmaceutically acceptable salt, solvate, metabolite, polymorph, ester, tautomer or prodrug thereof, either in vitro or in vivo.

The compound in the first aspect of this invention, or a pharmaceutically acceptable salt, solvate, metabolite, polymorph, ester, tautomer or prodrug thereof, has higher inhibitory activities on BTK than on ITK and exhibits excellent selectivities.

The compound in the first aspect of this invention, or a pharmaceutically acceptable salt, solvate, metabolite, polymorph, ester, tautomer or prodrug thereof, is highly inhibitorily effective on tumors with low toxicities.

BRIEF DESCRIPTION OF THE DRAWINGS

FIG. 1 shows comparison of the arthritis scores of the compounds of this invention and the reference compound.

DETAILED DESCRIPTION

This invention provides methods for inhibiting Bruton's tyrosine kinase in a subject in need thereof by administering to the subject thereof a composition containing a therapeutically effective amount of at least one compound having the structure of Formula (III). In some embodiments, the subject in need is suffering from an autoimmune disease, such as lupus and inflammatory bowel disease; from a heteroimmune condition or disease, such as greft versus host disease; from an inflammatory disease, such as asthma; from a cancer, such as diffuse large B cell lymphoma; from a thromboembolic disorder, such as myocardial infarct.

In some embodiments, any compound of Formula (III) may form a covalent bond with a cysteine residue on Bruton's tyrosine kinase.

In some embodiments, the irreversible Btk inhibitor compound used for the methods described herein inhibits the activity of Btk or a Btk homolog kinase with an in vitro $IC_{50}$ of less than 10 μM (e.g., less than 1 μM, less than 100 nM, less than 10 nM, less than 1 nM, less than 0.5 nM).

Described herein are compounds of Formula (III). Also described herein are pharmaceutically acceptable salts, pharmaceutically acceptable solvates, pharmaceutically active metabolites and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by Formula (III) are also provided.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated herein by reference in their entirety. In the event that there is a plurality of definitions for terms herein, those in this section prevail. Where reference is made to a URL or other such identifier or address, it is understood that such identifiers can change and interchange with particular information on the internet, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes" and "included" is not limiting. Likewise, use of the term "comprising" as well as other forms, such as "comprise", "comprises" and "comprised" is not limiting.

Definitions of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry and medicinal and pharmaceutical chemistry described herein are those known in the art. Standard techniques can be used for chemical syntheses, chemical analysis, pharmaceutical preparation, formulation and delivery, and treatment of patients. Standard techniques can be used for recombinant DNA, oligonucleotide synthesis and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed conventional methods well known in the art and as described in various general and more specific references that are cited and discussed throughout the present specification.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as, though not limited to, "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

It is to be understood that the methods and compositions described herein are not limited to the particular methodology, protocols, cell lines, constructs and reagents described herein and in this regard may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

The terms "moiety", "chemical moiety", "group" and "chemical group" refer to a specific segment or functional group of a molecule. Chemical moieties are often recognized chemical entities embedded in or appended to a molecule.

The terms "bond" or "single bond" refer to a chemical bond between two atoms, or two moieties when the atoms joined by the bond are considered to be part of a larger substructure.

The term "catalytic group" refers to a chemical functional group that assists catalysis by acting to lower the activation barrier to reaction.

The term "optional" or "optionally" means that the subsequently described event or circumstance may or may not occur, and that the description includes instances wherein said event or circumstance occurs and instances in which it does not. For example, "optionally substituted alkyl" means either "unsubstituted alkyl" (alkyl that is not substituted with a functioning group) or "substituted alkyl" (alkyl that is substituted with a functioning group) as defined below. Further, an optionally substituted group may be unsubstituted (e.g., $CH_2CH_3$), fully substituted (e.g., $CF_2CF_3$), mono-substituted (e.g., $CH_2CH_2F$) or substituted at a level anywhere in-between fully substituted and mono-substituted (e.g., $CH_2CHF_2$, $CF_2CH_3$, $CFHCHF_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituent described should generally be understood as having a maximum molecular weight of about 1,000 daltons, and more typically, up to about 500 daltons (except in those instances wherein macromolecular substituents are clearly intended, e.g., polypeptides, polysaccharides, polyethylene glycols, DNA, RNA and the like).

As used herein, includes $C_{1-x}$ includes $C_{1-2}$, $C_{1-3}$ ... $C_{1-x}$.

The term "alkyl" has the common meaning in the art.

The term "heteroalkyl" refers to optionally substituted alkyl structures, in which one or more of the skeletal chain carbon atoms (and any associated hydrogen atoms, as appropriate) are each independently replaced with a heteroatom (i.e. an atom other than carbon, such as, though not limited to, oxygen, nitrogen, sulfur, silicon, phosphorous, tin or combinations thereof).

The term "lower heteroalkyl" refers to a heteroalkyl having one to eight carbon atoms, preferably having one to six, or one to five, or one to four, or one to three, or one to two carbon atoms.

By way of example only, "$C_{1-4}$alkyl" indicates that there are one to four carbon atoms in the alky chain, e.g., the alkyl chain is selected from among methyl, ethyl, propyl, isopropyl, n-butyl, iso-butyl, sec-butyl and t-butyl. Thus, $C_{1-4}$alkyl includes $C_{1-2}$alkyl and $C_{1-3}$alkyl. Alkyl groups can be substituted or unsubstituted. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" wherein no numerical range is designated. The alkyl group could also be a "lower alkyl" having 1-6 carbon atoms, i.e., $C_{1-6}$ alkyl.

The term "non-cyclic alkyl" refers to an alkyl that is not cyclic, that is a straight or branched chain containing at least one carbon atom. Non-cyclic alkyls can be fully saturated or can contain non-cyclic alkenes and/or alkynes. Non-cyclic alkyls can be optionally substituted.

The term "alkylene" refers to a diradical derived from the above-defined monoradical, alkyl. Examples include, but are not limited to, methylene (—$CH_2$—), ethylene (—$CH_2CH_2$—), propylene (—$CH_2CH_2CH_2$—), isopropylene (—$CH(CH_3)CH_2$—) and the like.

The term "alkenyl" refers to a type of alkyl group in which the first two atoms of the alky group form a double bond that is not part of an aromatic group. That is, an alkenyl group begins with the atoms —C(R)=C(R)—R, wherein R refers to the remaining portions of the alkenyl group, which may be the same or different. Alkenyl groups could have 2 to 10 carbons. The alkenyl group could also be a "lower alkenyl" having 2 to 6 carbon atoms.

The term "alkenylene" refers to a diradical derived from the above-defined monoradical alkenyl. Examples include, but are not limited to, ethenylene (—CH=CH—), the propenylene isomers (e.g., —CH$_2$CH=CH— and —C(CH$_3$)=CH—) and the like.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. The "R" portion of the alkynyl moiety may be branched, straight chain or cyclic. Alkynyl groups can have 2 to 10 carbons. The alkynyl group could also be a "lower alkynyl" having 2 to 6 carbon atoms.

The term "alkynylene" refers to a diradical derived from the above-defined monoradical, alkynyl. Examples include, but are not limited to, ethynylene propynylene (—CH$_2$C≡C—) and the like.

The term "alkoxy" refers to an (alkyl)O-group, wherein alkyl is as defined herein.

The term "amide" is a chemical moiety with the formula —C(O)NHR or —NHC(O)R, wherein R is selected from among alkyl, cycloalkyl, aryl, heteroaryl and heteroalicyclic. An amide moiety may form a linkage between an amino acid or a peptide molecule and a compound described herein, thereby forming a prodrug.

The term "ester" refers to a chemical moiety with formula —COOR, wherein R is selected from among alkyl, cycloalkyl, aryl, heteroaryl and heteroalicyclic. Any hydroxyl, or carboxyl side chain on the compounds described herein can be esterified.

The term "ring" refers to any covalently closed structure. Ring include, for example, carbocycles, heterocycles, aromatics and non-aromatics. Ring can be optionally substituted. Rings can be monocyclic or polycyclic.

The term "membered ring" can embrace any cyclic structure. The term "membered" is meant to denote the number of skeletal atoms that constitute the ring. Thus, for example, pyridine and thiopyran are 6-membered rings and cyclophentyl and pyrrole are 5-membered rings.

The terms "carbocyclic" and "carbocycle" refer to a ring wherein each of the atoms forming the ring is a carbon atom. Carbocycle includes aryl and cycloalkyl. The term thus distinguishes carbocycle from heterocycle in which the ring backbone contains at least one atom which is different from carbon. Heterocycle includes heteroaryl and heterocycloalkyl. Carbocycles and heterocycles can be optionally substituted.

The term "aromatic" refers to a planar ring having a delocalized π-electron system containing 4n+2 π electrons, wherein n is an integer. Aromatic rings can be formed from five, six, seven, eight, nine, or more than nine atoms. Aromatics can be optionally substituted. This term "aromatic" includes both carbocyclic aryl and heterocyclic aryl groups. The more, this term "aromatic" also includes monocyclic or fused-ring polycyclic groups.

The term "aryl" refers to an aromatic ring wherein each of the atoms forming the ring is a carbon atom. Aryl ring can be formed by five, six, seven, eight, nine, or more than nine carbon atoms. Aryl groups can be optionally substituted. Examples of aryl groups include, but are not limited to, phenyl, naphthalenyl, phenanthrenyl, anthracenyl, fluorenyl and indenyl. Depending on the structure, an aryl group can be a monoradical or a diradical, i.e., arylene.

The term "cycloalkyl" refers to a monocyclic or polycyclic radical that contains only carbon and hydrogen, and may be saturated, partially unsaturated or fully unsaturated. Cycloalkyl groups include groups having from 3 to 10 ring atoms. Illustrative examples of cycloalkyl groups include the following moieties:

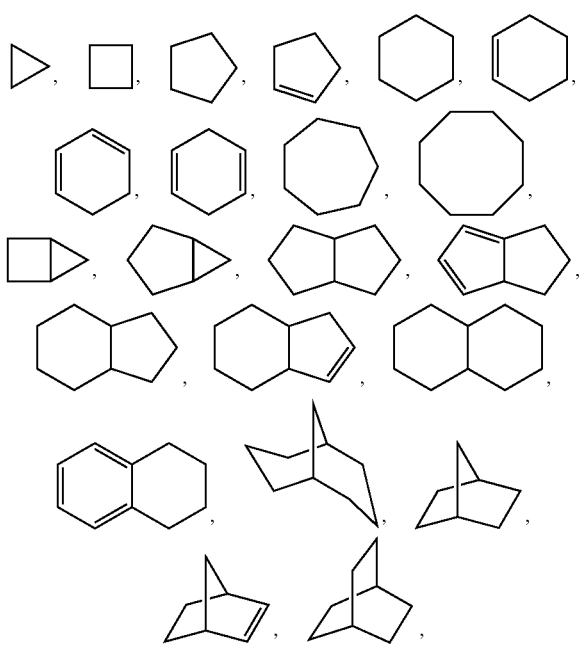

and so on. Depending on the structure, a cycloalkyl group can be a monoradical or a diradical. The cycloalkyl group could also be a "lower cycloalkyl" having 3 to 8 carbon atoms.

The terms "heterocycle" refers to heteroaromatic and heteroalicyclic groups containing one to four heteroatoms each selected from O, S and N, wherein each heterocyclic group has from 4 to 10 atoms in its ring system, with the proviso that the ring of said group does not contain two adjacent O or S atoms. Herein, whenever the number of carbon atoms in a heterocycle is indicated, at least one other atom must be present in the ring. Designations such as "$C_{1-6}$heterocycle" refer only to the number of carbon atoms in the ring and do not refer to the total number of atoms in the ring. It is understood that the heterocyclic ring can have additional heteroatoms in the ring. Designations such as "4-6 membered heterocycle" refer to the total number of atoms that are contained in the ring. In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their sing system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomor-pholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,4-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, pyrazolidinyl, imidazolinyl, imidazolidinyl, 3-azabicyclo [3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxzzolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxaziazolyl, thiadiazolyl, furazanyl, benzofurazanyl, benzothiophenyl, benzothiazolyl, benzoxazolyl, quinazolinyl, quinoxalinyl, naphthyridinyl and furopyridinyl.

The term "heteroaryl" refers to optionally substituted aromatic mono-radicals containing from about five to about twenty skeletal ring atoms, wherein one or more of the ring atoms is a heteroatom independently selected from among, but not limited to, oxygen, nitrogen, sulfur, phosphorous, silicon, selenium and tin; with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. In addition, the term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as an example, an imidiazole group may be attached to a parent molecule via any of its carbon atoms (imidazol-2-yl, imidazol-4-yl or imidazol-5-yl) or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings wherein the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyl, oxadiazolyl, indazolyl, pyridyl, pyridazyl, pyrimidyl, pyrazinyl, pyrrolyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide and the like.

The terms "non-aromatic heterocycle", "heterocycloalkyl" or "heteroalicyclic" refer to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioane, piperazine, 1,3-oxathiane, 1,4-oxathiin, 1,4-oxathiane, tetrahydro-1,4-thiazine, 2H-1,2-oxazine, maleimide, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine and 1,3-oxathiolane. Illustrative examples of heterocycloalkyl groups, also referred to as non-aromatic heterocycles, include:

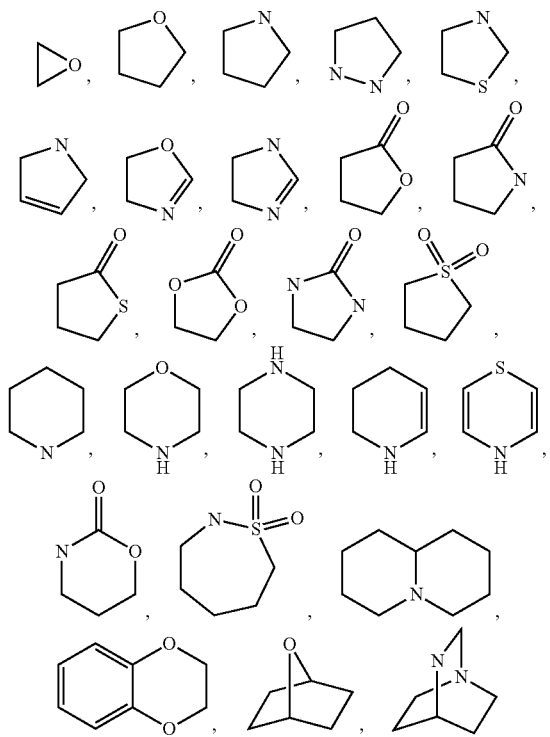

and the like.

The terms "halogen", "halo" or "halide" refer to fluoro, chloro, bromo and iodo.

The term "sulfinyl" refers to a diradical of —S(=O)—R.

The term "sulfonyl" refers to a diradical of —S(=O)$_2$—R.

The terms "sulfonamide", "sulfonamido" and "sulfonamidyl" refer to the groups of —S(O)$_2$NH— and —NHS(=O)$_2$—.

The term "cyano" refers to a group of formula —CN.

Certain Pharmaceutical Terminology

The term "Bruton's tyrosine kinase" refers to a Bruton's tyrosine kinase from *Homo sapiens*, as disclosed in, e.g., U.S. Pat. No. 6,326,469 (GenBank Accession No. NP_000052).

The term "Bruton's tyrosine kinase homolog" refers to orthologs of Bruton's tyrosine kinase, e.g., the orthologs from mouse (GenBank Accession No. AAB47246), dog (GenBank Accession No. XP_549139), rat (GenBank Accession No. NP_001007799), chicken (GenBank Accession No. NP_989564) or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEELYSSARQ").

The terms "preventing", "prevention" and "prevent" include reducing the likelihood of a patient incurring or developing autoimmune disease, heteroimmune disease, inflammatory disease, thromboembolic disorder or cancer (such as, diffuse large B-cell lymphoma, chronic lymphocytic lymphoma and B-cell prolymphocytic leukemia).

The term "subject", "patient" or "individual" refers to individuals suffering from a disease, a disorder, a condition, and the like, and encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs and cats; laboratory animals including rodents, such as rats, mice and guinea pigs, and the like. Examples of non-mammals include, but are not limited to, birds, fish, and the like. In one embodiment of the methods and compositions provided herein, the mammal is a human.

The terms "treat", "treating" and "treatment" and other grammatical equivalents include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the composition may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" refer to a sufficient amount of at least one agent or compound being administered which will relieve to some extent one or more of the symptoms of the disease or condition being treated. The result can be reduction and/or alleviation of the signs, symptoms or causes of a disease, or any other desired alteration of a biological system. For example, an "effective amount" for therapeutic uses is the amount of the composition comprising a compound as disclosed herein required to provide a clinically significant alleviation of a disease. An appropriate "effective" amount in any individual case may be determined using techniques, such as a dose escalation study.

The terms "administer", "administering", "administration", and the like, refer to the methods that may be used to enable delivery of a compound or a composition to the desired site of biological action. These methods include, but are not limited to, oral route, intraduodenal route, parenteral injection (including intravenous, subcutaneous, intraperitoneal, intramuscular, and intravascular or infusion), topical and rectal administrations. Those of skill in the art are familiar with administration techniques that can be employed for the compounds and methods described herein, e.g., as discussed in Goodman and Gilman, The Pharmacological Basis of Therapeutics, current ed.; Pergamon; and Remington's *Pharmaceutical Sciences* (current edition), Mack Publishing Co., Easton, Pa. In preferred embodiments, the compounds and compositions described herein are administered orally.

The term "acceptable" means having no persistent detrimental effect on the general health of the subject being treated.

The term "pharmaceutically acceptable" refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition" refers to a biologically active compound, optionally mixed with at least one pharmaceutically acceptable chemical component, such as, though not limited to, carriers, stabilizers, diluents, dispersing agents, suspending agents, thickening agents and/or excipients.

The term "carrier" refers to relatively nontoxic chemical compounds or agents that facilitate the incorporation of a compound into cells or tissues.

The term "agonist" refers to a molecule such as a compound, a drug, an enzyme activator or a hormone modulator which enhances the activity of another molecule or the activity of a receptor site.

The term "antagonist" refers to a molecule such as a compound, a drug, an enzyme inhibitor or a hormone modulator, which diminishes or prevents the action of another molecule or the activity of a receptor site.

The term "modulate" means to interact with a target either directly or indirectly so as to alter the activity of the target, including, by way of example only, to enhance the activity of the target, to inhibit the activity of the target, to limit the activity of the target, or to extend the activity of the target.

The term "modulator" refers to a molecule that interacts with a target either directly or indirectly. The interactions include, but are not limited to, the interactions of an agonist and an antagonist.

The term "pharmaceutically acceptable salt" refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including acetate, acrylate, adipate, alginate, aspartate, benzoate, benzenesulfonate, bisulfate, bisulfate, bromide, butyrate, butyn-1,4-dioate, camphorate, camphorsulfonate, caprylate, chlorobenzoate, chloride, citrate, cyclopentanepropionate, decanoate, gluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, y-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate, undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., J. Pharm. Sci. 1977, 66, 1-19). Furthermore, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium and aluminum salts and the like. Illustrative examples of bases include sodium hydroxide, potassium hydroxide, choline hydroxide, sodium carbonate, IV' ($C_{1-4}$ alkyl)$_4$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, the above reference of Berge et al.

The term "solvate" refers to a combination of a compound of this invention with a solvent molecule formed by solvation. In some embodiments, the solvate refers to a hydrate, e.g., the solvent molecule is a water molecule, the combination of a compound of this invention and water forms a hydrate.

The term "polymorph" or "polymorphism" refers to a compound of this invention present in different crystal lattice forms.

The term "ester" refers to a derivative of a compound of this invention derived from an oxoacid group and a hydroxyl group, either one of which can be present at the compound of this invention.

The term "tautomer" refers to an isomer readily interconverted from a compound of this invention by e.g., migration of a hydrogen atom or proton.

The term "pharmaceutically acceptable derivative or prodrug" refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

The terms "enhance" or "enhancing" means to increase or prolong either in potency or duration of a desired effect. Thus, in regard to enhancing the effect of a therapeutic agent, the term "enhancing" refers to the ability to increase or prolong, either in potency or duration, the effect of another therapeutic agent on a system.

An "enhancing-effective amount" refers to an amount adequate to enhance the effect of another therapeutic agent in a desired system.

The terms "pharmaceutical combination", "administering an additional therapy", "administering an additional therapeutic agent", and the like refer to a pharmaceutical therapy resulting from mixing or combining more than one active ingredient and includes both fixed and non-fixed combinations of the active ingredients. The term "fixed combination" means that at least one of the compounds described herein and at least one co-agent are both administered to a patient simultaneously in the form of a single entity or dosage. The term "non-fixed combination" means that at least one of the compounds described herein and at least one co-agent are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite" refers to a derivative of a compound which is formed when the compound is metabolized.

The term "active metabolite" refers to a biologically active derivative of a compound that is formed when the compound is metabolized.

The term "metabolized" refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

The term "Michael acceptor moiety" refers to a functional group that can participate in a Michael reaction, wherein a new covalent bond is formed between a portion of the Michael acceptor moiety and the donor moiety. The Michael acceptor moiety is an electrophile and the "donor moiety" is a nucleophile. The "G" groups presented in Formula (III) are non-limiting examples of Michael acceptor moieties.

The terms "nucleophile" and "nucleophilic" refer to an electron rich compound or a moiety thereof. An example of a nucleophile includes, but in no way is limited to, a cysteine residue of a molecule, such as, for example Cys 481 of Btk.

The terms "electrophile" and "electrophilic" refer to an electro poor or electron deficient molecule or a moiety thereof. Examples of electrophiles include, but in no way are limited to, Michael acceptor moieties.

The term "bioavailability" refers to the percentage of the weight of compounds disclosed herein, such as compounds of Formula (III), dosed that is delivered into the general circulation of the animal or human being studied. The total exposure ($AUC_{(0-\infty)}$) of a drug when administered intravenously is usually defined as 100% bioavailable (F %).

The term "oral bioavailability" refers to the extent to which compounds disclosed herein, such as compounds of Formula (III), are absorbed into the general circulation when the pharmaceutical composition is taken orally as compared to intravenous injection.

The term "blood plasma concentration" refers to the concentration of compounds disclosed herein, such as compounds of Formula (III), in the plasma component of blood of a subject. It is understood that the plasma concentration of compounds of Formula (III) may vary significantly between subjects, due to variability with respect to metabolism and/or possible interactions with other therapeutic agents. In accordance with one embodiment disclosed herein, the blood plasma concentration of the compounds of Formula (III) may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of a compound of Formula (III) may vary from subject to subject.

The term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The term "target protein" refers to a molecule or a portion of a protein capable of being bound by a selective binding compound. In certain embodiments, a target protein is Btk.

The term "$IC_{50}$" refers to an amount, concentration or dosage of a particular test compound that achieves a 50% inhibition of a maximal response, such as inhibition of Btk, in an assay that measures such response.

Compounds

The Btk inhibitor compounds described herein are selective for Btk and kinases having a cysteine residue in an amino acid sequence position of the tyrosine kinase that is homologous to the amino acid sequence position of cysteine 481 in Btk. The irreversible Btk inhibitor compound selectively and irreversibly inhibits an activated form of its target tyrosine kinase, such as a phosphorylated form of the tyrosine kinase.

Irreversible Btk inhibitor compounds can be used for the manufacture of a medicament for treating any of the foregoing conditions, such as autoimmune diseases, inflammatory diseases, allergy disorders, B-cell proliferative disorders or thromboembolic disorders. Inhibitor compounds described herein include a Michael acceptor moiety.

This invention provides a compound of Formula (III), or a pharmaceutically acceptable salt, solvate, metabolite, polymorph, ester, tautomer or prodrug thereof,

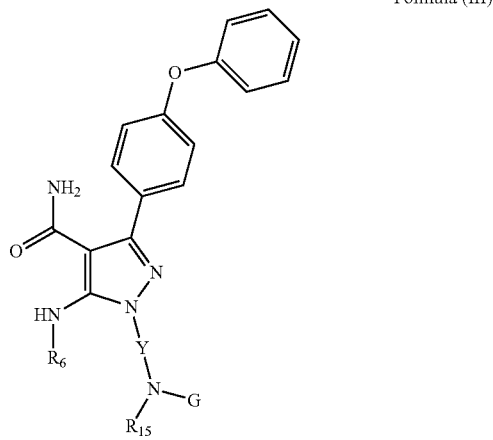

Formula (III)

wherein:

Y is selected from the group consisting of substituted or unsubstituted alkyl and a 4-, 5- or 6-membered cycloalkyl ring; and $R_{15}$ is selected from the group consisting of H and lower alkyl; or, Y and $R_{15}$ may join to form a 4-, 5- or 6-membered heterocyclic ring;

G is selected from the group consisting of H,

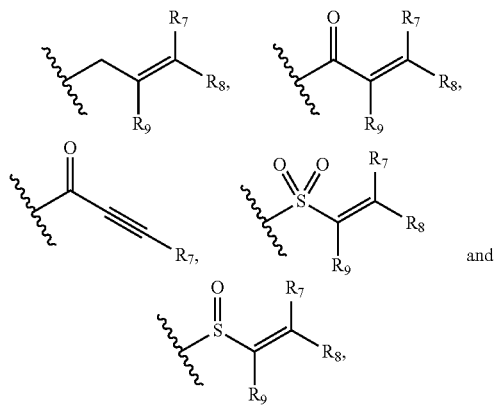

wherein $R_7$, $R_8$ and $R_9$ are each independently selected from the group consisting of H, halogen, —COOH, substituted or unsubstituted lower alkyl, and substituted or unsubstituted lower heteroalkyl;

$R_6$ is selected from the group consisting of H, —$C_{1-8}$alkyl, —$(CH_2)_nC_{3-7}$cycloalkyl, —$(CH_2)_nC_{2-9}$heterocycloalkyl, —(CH$_2$)$_n$—OH, —(CH$_2$)$_n$—(CHOH)$_n$—H, —(CH$_2$)$_n$—O—(CH$_2$)$_n$CH$_3$, —(CH$_2$)$_n$—S—(CH$_2$)$_n$CH$_3$, —(CH$_2$)$_n$—NH$_2$, —(CH$_2$)$_n$—NH(C$_{1-8}$alkyl), —(CH$_2$)$_n$—N(C$_{1-8}$alkyl)$_2$, —C(O)C$_{1-8}$alkyl;

N is 0, 1, 2, 3 or 4.

Methods for synthesizing the compounds described above are provided. In some embodiments, the compounds described herein can be prepared by the methods described below. The procedures and examples below are intended to illustrate those methods. Neither the procedures nor the examples should be construed as limiting the invention in any way. Compounds described herein may also be synthesized using standard synthetic techniques known to those of skill in the art or using methods known in the art in combination with methods described herein.

SYNTHETIC METHODS AND EXAMPLES

Scheme 1

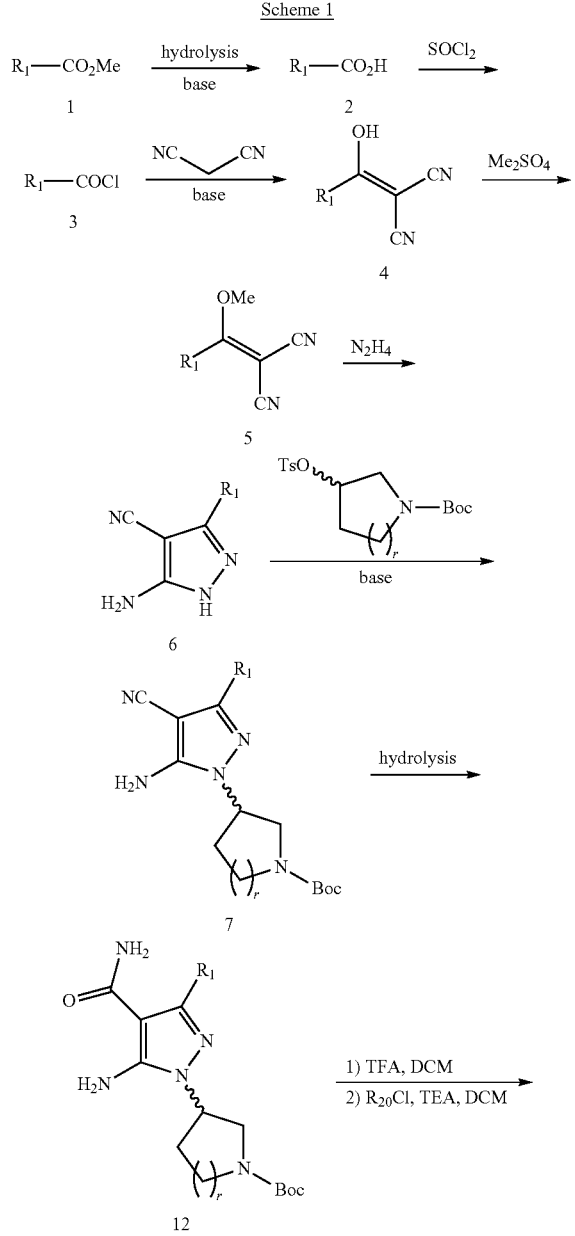

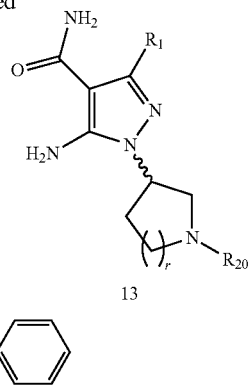

$r = 1\text{-}2, R_1 =$ [4-phenoxyphenyl group]

Compounds of formula (III) of the present invention can be prepared according to the routes shown in Scheme 1. The products of the reactions in Scheme 1 can be obtained using conventional separation techniques, including, but not limited to, filtration, distillation, crystallization, chromatography and the like. The starting material used for the synthesis may be synthesized or can be obtained from commercial sources, such as, but not limited to, Aldrich or Sigma. Such materials may be characterized using conventional means, including to physical constants and spectral data. Compounds described herein may be prepared using the synthetic methods described herein as a single isomer or a mixture of isomers.

The starting material 1 was purchased from commercial sources directly or obtained through organic synthesis. Hydrolysis of 1 using a base, such as NaOH in EtOH/H$_2$O at 70° C. for 1 h gives intermediate 2, which was directly refluxed in sulfurous dichloride to give intermediate 3, which was directly used in the next step. Malononitrile was reacted with intermediate 3 under the action of a base, such as NaH, in THF at 0° C. in an ice-water bath to get intermediate 4, which was methylated with dimethyl sulfate to give intermediate 5. Hydrazine hydrate was reacted with intermediate 5 to give the important intermediate 6, which is an important entry into the synthesis of compounds of Formula (III) of the present invention. Base (such as Cs$_2$CO$_3$ in DMF) mediated SN$_2$ reaction was carried out between intermediate 6 and Ts-protected N-Boc-3-hydroxypiperdine to give intermediate 7. Intermediate 7 was hydrolyzed with, for example, concentrated sulfuric acid/base/hydrogen peroxide or DEPO, to give compound 12 in relatively high yield. Finally, trifluoro acetic acid was used for the deprotection followed by the coupling reaction with acryloyl chloride to provide the final product 13.

The dosage for obtaining necessary therapeutic effects is conveniently from 0.01 to 3 milligram/kilogram body weight, preferably from 0.1 to 1 milligram/kilogram body weight of the compound of the present invention for intravenous administration; and from 0.1 to 8 milligram/kilogram body weight, preferably from 0.5 to 3 milligram/kilogram body weight of the compound of the present invention for oral administration, 1 to 3 times per day in each case. The compound prepared according to the present invention can be administered by intravenous injection, subcutaneous injection, intramuscular injection, rectal administration, nasal drops, inhalation, transdermal or oral administration, wherein aerosol is particularly suitable for inhalation. They can also be formulated into conventional pharmaceutical preparations, such as tablets, enteric coated tablets, capsules, powders, suspension, solution, metered aerosol or suppository. If appropriate, one or more conventional inert carriers and/or diluents, such as corn starch, lactose, sucrose, microcrystalline cellulose, magnesium stearate, polyvinylpyrrolidone, citric acid, tartaric acid, water, water, water/ethanol, water/glycerol, water/sorbitol, water/polyethyleneglycol, propylene glycol, cetyl stearyl ethanol, carboxymethyl cellulose or fatty substance, such as hardened fat, or an appropriate mixture thereof, can be added.

Example 1

(R)-5-amino-3-(4-phenoxyphenyl)-1-(1-(vinylsulfonyl)piperidin-3-yl)-1H-pyrazole-4-carboxamide

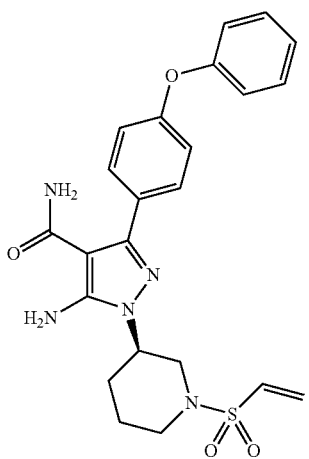 [SMILES: C=CS(=O)(=O)N1CCC[C@@H](n2nc(-c3ccc(Oc4ccccc4)cc3)c(C(N)=O)c2N)C1]

Step A: Methyl 4-Phenoxybenzoate

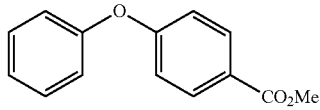

To a flask filled with 200 mL of DMF were added methyl 4-iodobenzoate (80 g, 1.0 eq) and phenol (34.5 g, 1.2 eq) at room temperature, and to the reaction mixture were added K₂CO₃ (84 g, 2.0 eq), CuI (11.6 g, 20%) and N,N-Dimethylglycine (12.6 g, 40%). After completion of addition, the reaction mixture was stirred overnight at 110° C. After completion of the reaction, the mixture was cooled to room temperature, water was added, and the mixture was extracted with EtOAc. The organic layer was washed with water and brine, dried over anhydrous Na₂SO₄, and isolated with column chromatograph to provide the product as a white solid (45 g, 65%).

¹H NMR (400 MHz, CDCl₃) δ 7.99-8.01 (m, 2H), 7.37-7.41 (m, 2H), 7.17-7.21 (m, 1H), 7.05-7.08 (m, 2H), 6.97-7.00 (m, 2H), 3.90 (s, 3H).

Step B: 4-Phenoxybenzoic Acid

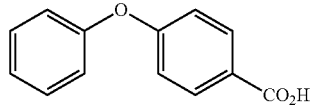 [SMILES: O=C(O)c1ccc(Oc2ccccc2)cc1]

To a flask filled with 100 mL of ethanol was added methyl 4-phenoxybenzoate (20 g, 1.0 eq) at room temperature, and then a solution of NaOH (7 g, 2.0 eq) in water (50 mL) was added slowly. After completion of addition, the reaction mixture was stirred at 70° C. for 15 minutes. After completion of the reaction, the mixture was cooled to room temperature, and the ethanol solvent was removed by rotate-evaporation. Diluted HCl acid was added to adjust the pH to 2-3, and the mixture was stirred at room temperature for 5 minutes. The white solid thus formed was collected and dried to provide the product (16 g, 85%).

¹H NMR (400 MHz, CDCl₃) δ 8.06-8.09 (m, 2H), 7.39-7.43 (m, 2H), 7.19-7.23 (m, 1H), 7.07-7.10 (m, 2H), 7.00-7.03 (m, 2H).

Step C: 4-Phenoxybenzoyl Chloride

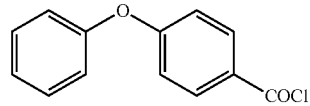 [SMILES: O=C(Cl)c1ccc(Oc2ccccc2)cc1]

To a flask filled with 50 mL thionyl chloride in an ice-bath was slowly added 4-phenoxybenzoic acid (8 g, 1.0 eq). After completion of addition, the reaction mixture was refluxed at 70° C. for 3 hours. After completion of the reaction, the mixture was cooled to room temperature, thionyl chloride was removed by rotate-evaporation, toluene was added, and the solvent was again removed by rotate-evaporation; the same procedure was repeated 3 times to provide an oil, which was used directly in the next step without being further purified (8.65 g, 98%).

¹H NMR (400 MHz, CDCl₃) δ 8.07-8.09 (m, 2H), 7.41-7.45 (m, 2H), 7.23-7.27 (m, 1H), 7.08-7.11 (m, 2H), 7.00-7.02 (m, 2H).

Step D:
2-(hydroxy(4-phenoxyphenyl)methylene)malononitrile

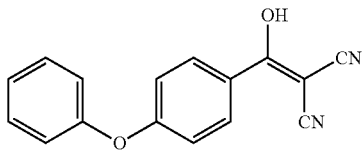 [SMILES: N#CC(C#N)=C(O)c1ccc(Oc2ccccc2)cc1]

To a three-neck flask filled with a solution of malononitrile (2.7 g, 1.1 eq) in dry THF (250 mL) was slowly added NaH (1.64 g, 60%, 1.1 eq). After completion of addition, the mixture was warmed up to room temperature and stirred for 10 minutes. The reaction mixture was then cooled to 0° C. and a solution of 4-phenoxybenzoyl chloride (8.65 g, 1.0 eq) in THF was added. After completion of addition, the reaction mixture was stirred overnight at room temperature. After completion of the reaction, small amount of water was added to quench the reaction, THF was removed using rotate evaporation, and the mixture was extracted with EtOAc. The organic phase was washed with water and brine, dried over anhydrous Na₂SO₄, and isolated through silica gel column chromatography to provide the product as a solid (3.6 g, 37%).

¹H NMR (400 MHz, DMSO) δ 7.60-7.64 (m, 2H), 7.40-7.44 (m, 2H), 7.16-7.20 (m, 1H), 7.05-7.07 (m, 2H), 6.92-6.96 (m, 2H).

Step E: 2-(methoxy(4-phenoxyphenyl)methylene)malononitrile

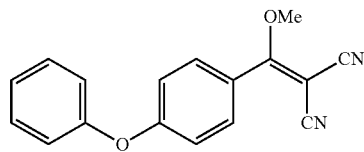

To a mixed solvent of 1:1 (v/v) dioxane/H₂O (50 mL) at room temperature was added 2-(hydroxy(4-phenoxyphenyl)methylene)malononitrile (3.6 g, 1.0 eq) followed by slow addition of Me₂SO₄ (2.6 g, 1.5 eq). After completion of addition, the reaction mixture was heated to 80° C. and stirred for 3 hours. After completion of the reaction, the solvent was removed with rotate evaporation, water was added, and the mixture was extracted with EtOAc. The organic phase was washed with water and brine, dried over anhydrous Na₂SO₄, and isolated through silica gel column chromatography to provide the product as a colorless oil (2.7 g, 72%).

¹H NMR (400 MHz, CDCl₃) δ 7.48-7.51 (m, 2H), 7.41-7.45 (m, 2H), 7.25-7.27 (m, 1H), 7.07-7.11 (m, 4H), 3.99 (s, 3H).

Step F: 5-amino-3-(4-phenoxyphenyl)-1H-pyrazole-4-carbonitrile

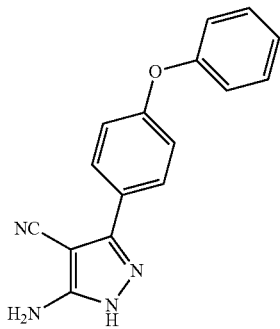 [SMILES: N#Cc1c(-c2ccc(Oc3ccccc3)cc2)n[nH]c1N]

To 50 mL of EtOH at room temperature was added 2-(methoxy(4-phenoxyphenyl) methylene)malononitrile (1 g, 1.0 eq) followed by slow addition of hydrazine hydrate (0.5 g, 85%, 2.0 eq). After completion of addition, the reaction mixture was heated to 90° C. and refluxed for 4 hours. After completion of the reaction, the mixture was cooled to room temperature, and the solvent was removed with rotate evaporation. Water (50 mL) was added and the mixture was stirred at room temperature for 5 minutes. The white solid thus precipitated was collected and dried as the product (1.0 g, 99%).

¹H NMR (400 MHz, DMSO) δ 7.78-7.81 (m, 2H), 7.40-7.44 (m, 2H), 7.16-7.20 (m, 1H), 7.06-7.11 (m, 4H), 6.26 (brs, 2H).

Step G: tert-butyl (R)-3-(5-amino-4-cyano-3-(4-phenoxyphenyl)-1H-pyrazol-1-yl)piperidine-1-carboxylate

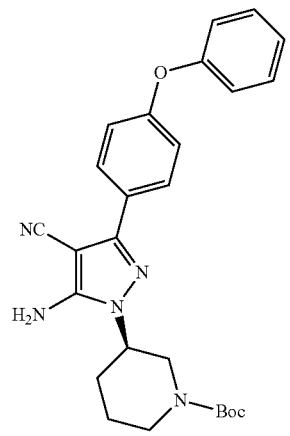 [SMILES: CC(C)(C)OC(=O)N1CCC[C@@H](n2nc(-c3ccc(Oc4ccccc4)cc3)c(C#N)c2N)C1]

Tert-butyl (S)-3-(tosyloxy)piperidine-1-carboxylate: To 50 mL of CH₂Cl₂ in an ice bath was added tert-butyl (S)-3-hydroxypiperidine-1-carboxylate (3 g, 1.0 eq) followed by slow addition of 4-methylbenzenesulfonyl chloride (3.4 g, 1.2 eq), N,N-dimethylpyridin-4-amine (0.1 g, 10%) and triethylamine (3 g, 2.0 eq). After completion of addition, the reaction mixture was warmed up to room temperature and stirred overnight. The organic phase was washed with water and brine, dried over anhydrous Na₂SO₄, and isolated through silica gel column chromatography to provide the product as a white solid (4.9 g, 93%).

¹H NMR (400 MHz, CDCl₃) δ 67.80 (d, J=8.0 Hz, 2H), 7.34 (d, J=8.0 Hz, 2H), 4.46 (brs, 1H), 3.54-3.58 (m, 1H), 3.31-3.40 (m, 3H), 2.45 (s, 3H), 1.80-1.88 (m, 1H), 1.65-1.79 (m, 2H), 1.47-1.52 (m, 1H), 1.43 (s, 9H).

To 30 mL of dry DMF at room temperature were added tert-butyl (S)-3-(tosyloxy) piperidine-1-carboxylate (0.77 g, 1.2 eq) and 5-amino-3-(4-phenoxyphenyl)-1H-pyrazole-4-carbonitrile (0.5 g, 1.0 eq) and then Cs₂CO₃ solid (1.18 g, 2.0 eq) was added to the reaction mixture. After completion of addition, the reaction system was heated to 80° C. and stirred at this temperature for 5 hours. After completion of the reaction, the mixture was cooled to room temperature, water was added, and the mixture was extracted with EtOAc. The organic phase was washed with water and brine, dried over anhydrous Na₂SO₄, and isolated through silica gel column chromatography to provide product 7 as a white solid (0.25 g, 30%).

¹H NMR (400 MHz, CDCl₃) δ 7.85-7.88 (m, 2H), 7.33-7.37 (m, 2H), 7.09-7.14 (m, 1H), 7.03-7.06 (m, 4H), 4.52 (brs, 2H), 4.19-4.29 (m, 1H), 4.01-4.18 (m, 1H), 3.80-3.89 (m, 1H), 3.02-3.19 (m, 1H), 2.81 (t, J=12.8 Hz, 1H), 2.20-2.31 (m, 1H), 2.07-2.18 (m, 1H), 1.83-1.92 (m, 1H), 1.76-1.81 (m, 1H), 1.44 (s, 9H).

Step H: tert-butyl (R)-3-(5-amino-4-carbamoyl-3-(4-phenoxyphenyl)-1H-pyrazol-1-yl)piperidine-1-carboxylate

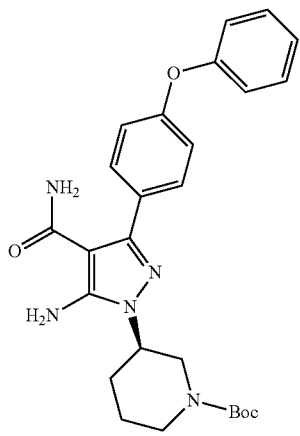 [SMILES: CC(C)(C)OC(=O)N1CCC[C@@H](n2nc(-c3ccc(Oc4ccccc4)cc3)c(C(N)=O)c2N)C1]

To 5 mL of DMSO were added tert-butyl (R)-3-(5-amino-4-cyano-3-(4-phenoxyphenyl)-1H-pyrazol-1-yl)piperidine-1-carboxylate (0.2 g, 1.0 eq) and $K_2CO_3$ solid (0.18 g, 3.0 eq) at room temperature. Then hydrogen peroxide (8 mL, 30%) was added. After completion of addition, the reaction system was heated to 60° C. and stirred at this temperature for 5 hours. After completion of the reaction, the mixture was cooled to room temperature. Water was added, and the mixture was extracted with $CH_2Cl_2$. The organic phase was washed with water and brine, dried over anhydrous $Na_2SO_4$, and isolated through silica gel column chromatography to provide the product as a white solid (0.2 g, 97%).

$^1$H NMR (400 MHz, $CDCl_3$) δ 7.48-7.52 (m, 2H), 7.35-7.39 (m, 2H), 7.13-7.17 (m, 1H), 7.04-7.08 (m, 4H), 5.54 (s, 2H), 5.19 (brs, 2H), 4.19-4.28 (m, 1H), 4.07-4.15 (m, 1H), 3.81-3.90 (m, 1H), 3.03-3.21 (m, 1H), 2.75 (t, J=11.6 Hz, 1H), 2.09-2.29 (m, 2H), 1.81-1.92 (m, 1H), 1.51-1.68 (m, 1H), 1.45 (s, 9H).

Step I: (R)-5-amino-3-(4-phenoxyphenyl)-1-(piperidin-3-yl)-1H-pyrazole-4-carboxamide

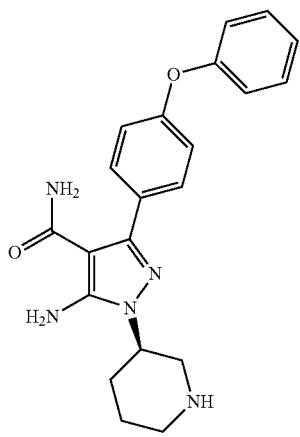 [SMILES: NC(=O)c1c(-c2ccc(Oc3ccccc3)cc2)nn([C@@H]2CCCNC2)c1N]

To 20 mL of $CH_2Cl_2$ was added tert-butyl (R)-3-(5-amino-4-carbamoyl-3-(4-phenoxyphenyl)-1H-pyrazol-1-yl)piperidine-1-carboxylate (0.2 g, 1.0 eq) at room temperature, followed by slow addition of trifluoro acetic acid (1 mL). After completion of addition, the reaction mixture was stirred at room temperature for 2 hours. Water was added, and the mixture was extracted with $CH_2Cl_2$. The organic phase was washed with water and brine, dried over anhydrous $NaSO_4$, and isolated through silica gel column chromatograph to provide the product as a white solid (0.1 g, 63%).

$^1$H NMR (400 MHz, $CDCl_3$) δ 67.26-7.34 (m, 4H), 7.10-7.13 (m, 1H), 6.93-7.01 (m, 4H), 6.49 (s, 2H), 5.25 (brs, 2H), 4.65-4.72 (m, 1H), 3.71-3.82 (m, 1H), 3.42-3.51 (m, 1H), 3.21-3.29 (m, 1H), 2.80-2.91 (m, 1H), 1.91-2.06 (m, 4H). m/z=378 [M+1]$^+$.

Step J: (R)-5-amino-3-(4-phenoxyphenyl)-1-(1-(vinylsulfonyl)piperidin-3-yl)-1H-pyrazole-4-carboxamide

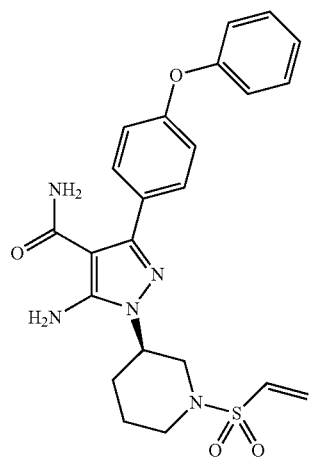 [SMILES: C=CS(=O)(=O)N1CCC[C@@H](n2nc(-c3ccc(Oc4ccccc4)cc3)c(C(N)=O)c2N)C1]

To 10 mL of $CH_2Cl_2$ in an ice bath were added (R)-5-amino-3-(4-phenoxy-phenyl)-1-(piperidin-3-yl)-1H-pyrazole-4-carboxamide (0.85 g, 1.0 eq) and triethyl amine (45 mg, 2.0 eq) followed by slow addition of ethenesulfonyl chloride (28 mg, 1.0 eq). After completion of addition, the reaction mixture was stirred in the ice bath for 5 minutes. After completion of the reaction, water was added, and the mixture was extracted with $CH_2Cl_2$. The organic phase was washed with water and brine, dried over anhydrous $Na_2SO_4$, and isolated through silica gel column chromatography to provide the product as a white solid (0.08 g, 85%).

$^1$H NMR (400 MHz, $CDCl_3$) δ 7.49-7.52 (m, 2H), 7.35-7.39 (m, 2H), 7.14-7.18 (m, 1H), 7.04-7.09 (m, 4H), 6.58-6.62 (m, 1H), 6.35 (d, J=16.4 Hz, 1H), 5.70-5.77 (m, 2.5H), 5.48 (s, 0.5H), 5.20 (brs, 2H), 4.82 (d, J=12.8 Hz, 0.5H), 4.61-4.68 (m, 0.5H), 4.11-4.19 (m, 0.5H), 4.01 (d, J=12.8 Hz, 0.5H), 3.82-3.94 (m, 1H), 3.55-3.68 (m, 0.5H), 3.00-3.19 (m, 1H), 2.64-2.78 (m, 0.5H), 2.30-2.42 (m, 1H), 2.14-2.22 (m, 1H), 1.91-2.01 (m, 1H), 1.60-1.69 (m, 1H). m/z=468 [M+1]$^+$.

Example 2

(R)-5-amino-3-(4-phenoxyphenyl)-1-(1-(vinylsulfonyl)pyrrolidin-3-yl)-1H-pyrazole-4-carboxamide

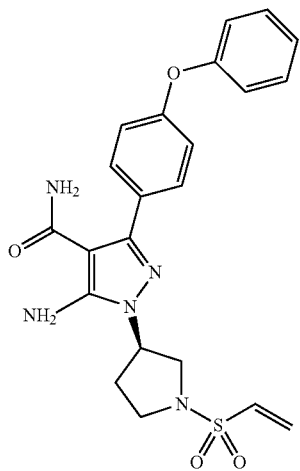 [SMILES: C=CS(=O)(=O)N1CC[C@@H](n2nc(-c3ccc(Oc4ccccc4)cc3)c(C(N)=O)c2N)C1]

The synthesis of Example 2 was accomplished using a procedure analogous to that described in Example 1 with tert-butyl (S)-3-(tosyloxy)pyrrolidine-1-carboxylate.

$^1$H NMR (400 MHz, CDCl$_3$) δ 7.48 (d, J=8.4 Hz, 2H), 7.39 (t, J=7.6 Hz, 2H), 7.18 (t, J=7.6 Hz, 1H), 7.06-7.09 (m, 4H), 6.51 (dd, J=16.8, 10.0 Hz, 1H), 6.25 (d, J=16.4 Hz, 1H), 5.89 (d, J=10.0 Hz, 1H), 5.52 (s, 2H), 5.10-5.30 (brs, 2H), 4.67-4.71 (m, 1H), 3.73-3.82 (m, 2H), 3.51-3.60 (m, 2H), 2.50-2.58 (m, 1H), 2.37-2.44 (m, 1H). m/z=454 [M+1]$^+$.

Example 3

(R,E)-5-amino-1-(1-(4-(dimethylamino)but-2-enoyl)pyrrolidin-3-yl)-3-(4-phenoxyphenyl)-1H-pyrazole-4-carboxamide

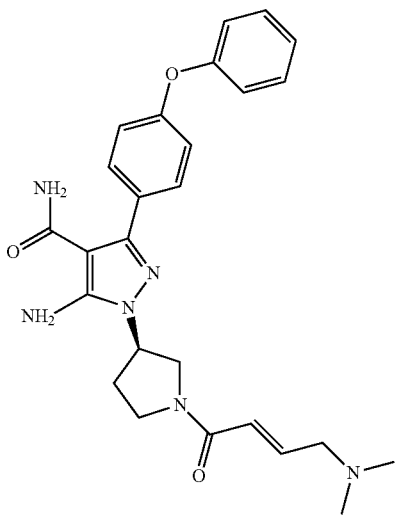 [SMILES: CN(C)C/C=C/C(=O)N1CC[C@@H](n2nc(-c3ccc(Oc4ccccc4)cc3)c(C(N)=O)c2N)C1]

The synthesis of Example 3 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.47-7.50 (m, 2H), 7.37 (t, J=7.6 Hz, 2H), 7.15 (t, J=7.6 Hz, 1H), 7.04-7.08 (m, 4H), 6.88-6.97 (m, 1H), 6.27 (dd, J=17.2, 11.6 Hz, 1H), 5.55 (s, 1H), 5.51 (s, 1H), 5.15-5.35 (brs, 2H), 4.63-4.71 (m, 1H), 3.90-4.06 (m, 3H), 3.57-3.75 (m, 1H), 3.07-3.10 (m, 2H), 2.68-2.77 (m, 0.5H), 2.53-2.58 (m, 0.5H), 2.28-2.45 (m, 1H), 2.26 (s, 3H), 2.24 (s, 3H). m/z=475 [M+1]$^+$.

Example 4

(R,E)-5-amino-1-(1-(4-morpholinobut-2-enoyl)pyrrolidin-3-yl)-3-(4-phenoxyphenyl)-1H-pyrazole-4-carboxamide

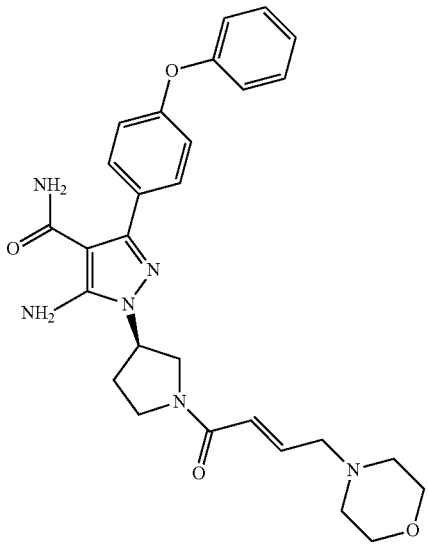 [SMILES: NC(=O)c1c(-c2ccc(Oc3ccccc3)cc2)nn([C@@H]2CCN(C(=O)/C=C/CN3CCOCC3)C2)c1N]

The synthesis of Example 4 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.47-7.50 (m, 2H), 7.37 (t, J=8.4 Hz, 2H), 7.16 (t, J=7.6 Hz, 1H), 7.05-7.09 (m, 4H), 6.88-6.95 (m, 1H), 6.27-6.36 (m, 1H), 5.52 (s, 1H), 5.47 (s, 1H), 5.13-5.37 (brs, 2H), 4.57-4.77 (m, 1H), 3.89-4.09 (m, 3H), 3.61-3.76 (m, 5H), 3.13-3.18 (m, 2H), 2.69-2.79 (m, 0.5H), 2.36-2.60 (m, 5.5H). m/z=517 [M+1]$^+$.

Example 5

(R,E)-5-amino-3-(4-phenoxyphenyl)-1-(1-(4-(piperidin-1-yl)but-2-enoyl)pyrrolidin-3-yl)-1H-pyrazole-4-carboxamide

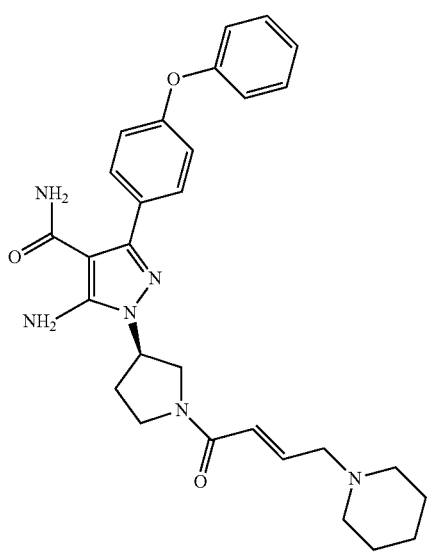 [SMILES: NC(=O)c1c(-c2ccc(Oc3ccccc3)cc2)nn([C@@H]2CCN(C(=O)/C=C/CN3CCCCC3)C2)c1N]

The synthesis of Example 5 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.45-7.48 (m, 2H), 7.35 (t, J=7.6 Hz, 2H), 7.14 (t, J=7.6 Hz, 1H), 7.03-7.06 (m, 4H), 6.84-6.92 (m, 1H), 6.41-6.52 (m, 1H), 5.54 (s, 1H), 5.51 (s, 1H), 5.12-5.30 (brs, 2H), 4.62-4.74 (m, 1H), 3.85-4.14 (m, 3H), 3.69-3.78 (m, 0.5H), 3.59-3.66 (m, 0.5H), 3.24-3.36 (m, 2H), 2.55-2.79 (m, 5H), 2.28-2.44 (m, 1H), 1.66-1.79 (m, 4H), 1.44-1.57 (m, 2H). m/z=515 [M+1]$^+$.

Example 6

(R,E)-5-amino-3-(4-phenoxyphenyl)-1-(1-(4-(pyrrolidin-1-yl)but-2-enoyl)pyrrolidin-3-yl)-1H-pyrazole-4-carboxamide

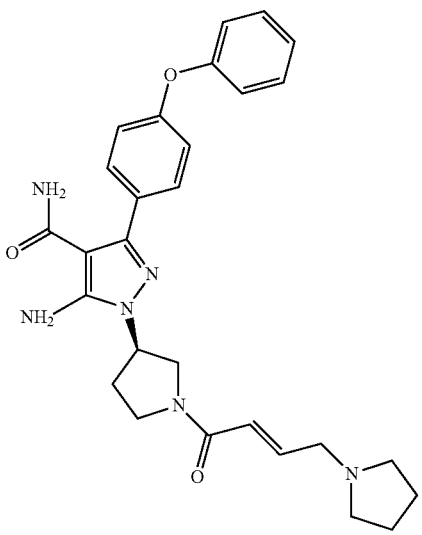 [SMILES: NC(=O)c1c(-c2ccc(Oc3ccccc3)cc2)nn([C@@H]2CCN(C(=O)/C=C/CN3CCCC3)C2)c1N]

The synthesis of Example 6 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.47-7.50 (m, 2H), 7.37 (t, J=7.6 Hz, 2H), 7.15 (t, J=7.6 Hz, 1H), 7.04-7.08 (m, 4H), 6.86-6.97 (m, 1H), 6.46 (d, J=15.2 Hz, 1H), 5.71 (s, 1H), 5.58 (s, 1H), 5.12-5.37 (brs, 2H), 4.60-4.85 (m, 1H), 3.86-4.14 (m, 3H), 3.60-3.78 (m, 1H), 3.35-3.54 (m, 2H), 2.69-2.86 (m, 4.5H), 2.51-2.64 (m, 0.5H), 2.25-2.46 (m, 1H), 1.81-1.96 (m, 4H). m/z=501 [M+1]$^+$.

Example 7

(R,E)-5-amino-1-(1-(but-2-enoyl)pyrrolidin-3-yl)-3-(4-phenoxyphenyl)-1H-pyrazole-4-carboxamide

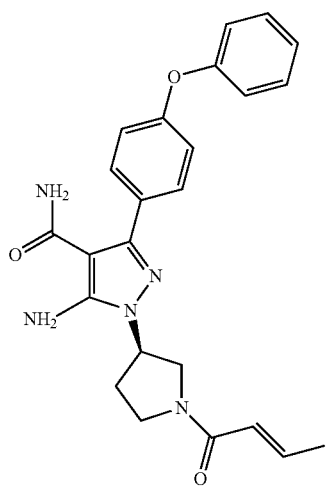 [SMILES: C/C=C/C(=O)N1CC[C@@H](n2nc(-c3ccc(Oc4ccccc4)cc3)c(C(N)=O)c2N)C1]

The synthesis of Example 7 was accomplished using a procedure analogous to that described in Example 1 with (R)-5-amino-3-(4-phenoxyphenyl)-1-(pyrrolidin-3-yl)-1H-pyrazole-4-carboxamide.

¹H NMR (400 MHz, CDCl₃) δ 7.47-7.50 (m, 2H), 7.35-7.39 (m, 2H), 7.14-7.18 (m, 1H), 7.05-7.09 (m, 4H), 6.92-6.98 (m, 1H), 6.11 (dd, J=14.0, 24.4 Hz, 1H), 5.55 (s, 1H), 5.51 (s, 1H), 5.22 (brs, 2H), 4.62-4.70 (m, 1H), 3.88-4.04 (m, 3H), 3.64-3.70 (m, 1H), 2.30-2.87 (m, 2H), 1.86-1.90 (m, 3H). m/z=432 [M+1]⁺.

Example 8

(R,E)-5-amino-1-(1-(4-methylpent-2-enoyl)pyrrolidin-3-yl)-3-(4-phenoxyphenyl)-1H-pyrazole-4-carboxamide

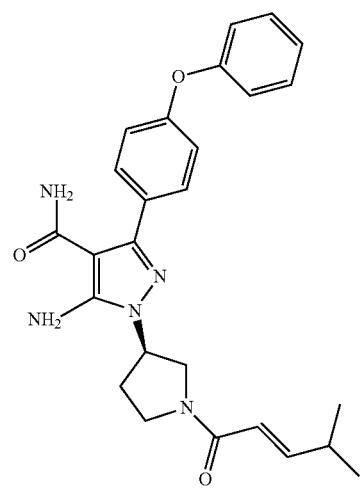 [SMILES: CC(C)/C=C/C(=O)N1CC[C@@H](n2nc(-c3ccc(Oc4ccccc4)cc3)c(C(N)=O)c2N)C1]

The synthesis of Example 8 was accomplished using a procedure analogous to that described in Example 1 with (R)-5-amino-3-(4-phenoxyphenyl)-1-(pyrrolidin-3-yl)-1H-pyrazole-4-carboxamide.

¹H NMR (400 MHz, CDCl₃) δ 7.48-7.51 (m, 2H), 7.35-7.39 (m, 2H), 7.14-7.17 (m, 1H), 7.04-7.09 (m, 4H), 6.92 (dd, J=6.4, 14.8 Hz, 1H), 6.02 (dd, J=15.2, 24.8 Hz, 1H), 5.52 (s, 1H), 5.48 (s, 1H), 5.20 (brs, 2H), 4.60-4.70 (m, 1H), 3.90-4.04 (m, 3H), 3.60-3.74 (m, 1H), 2.30-2.88 (m, 3H), 1.04-1.07 (m, 6H). m/z=460 [M+1]⁺.

Example 9

(R,E)-5-amino-1-(1-(4-methoxybut-2-enoyl)pyrrolidin-3-yl)-3-(4-phenoxyphenyl)-1H-pyrazole-4-carboxamide

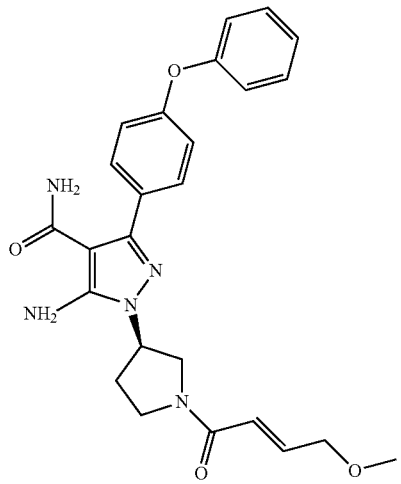 [SMILES: COC/C=C/C(=O)N1CC[C@@H](n2nc(-c3ccc(Oc4ccccc4)cc3)c(C(N)=O)c2N)C1]

The synthesis of Example 9 was accomplished using a procedure analogous to that described in Example 1 with (R)-5-amino-3-(4-phenoxyphenyl)-1-(pyrrolidin-3-yl)-1H-pyrazole-4-carboxamide.

¹H NMR (400 MHz, CDCl₃) δ 7.47-7.50 (m, 2H), 7.35-7.39 (m, 2H), 7.13-7.17 (m, 1H), 7.05-7.09 (m, 4H), 6.94 (dd, J=4.0, 14.8 Hz, 1H), 6.36 (dd, J=7.2, 23.2 Hz, 1H), 5.55 (s, 1H), 5.52 (s, 1H), 5.23 (brs, 2H), 4.62-4.74 (m, 1H), 3.97-4.11 (m, 5H), 3.60-3.78 (m, 1H), 3.41 & 3.38 (s, 3H), 2.30-2.78 (m, 2H). m/z=462 [M+1]⁺.

Example 10

(R,E)-4-(3-(5-amino-4-carbamoyl-3-(4-phenoxyphenyl)-1H-pyrazol-1-yl)pyrrolidin-1-yl)but-2-enoic Acid

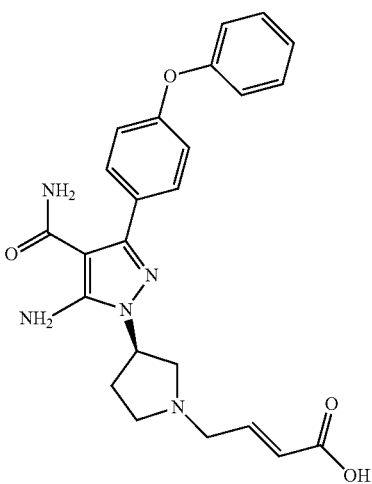 [SMILES: NC(=O)c1c(-c2ccc(Oc3ccccc3)cc2)nn([C@@H]2CCN(C/C=C/C(=O)O)C2)c1N]

The synthesis of Example 10 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.44 (d, J=8.0 Hz, 2H), 7.34 (t, J=8.0 Hz, 2H), 7.10-7.20 (m, 3H), 7.10-7.04 (m, 4H), 6.87-6.94 (m, 1H), 5.92 (d, J=14.8 Hz, 1H), 5.40-5.56 (brs, 2H), 4.97-5.04 (m, 1H), 3.46-3.58 (m, 1H), 3.16-3.38 (m, 2H), 2.95-3.10 (m, 1H), 2.35-2.55 (m, 2H), 2.19-2.33 (m, 2H). m/z=448 [M+1]$^+$.

Example 11

(R,Z)-4-(3-(5-amino-4-carbamoyl-3-(4-phenoxyphenyl)-1H-pyrazol-1-yl)pyrrolidin-1-yl)-4-oxobut-2-enoic Acid

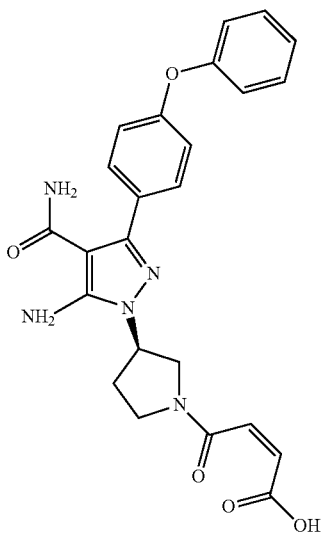 [SMILES: NC(=O)c1c(-c2ccc(Oc3ccccc3)cc2)nn([C@@H]2CCN(C(=O)/C=C\C(=O)O)C2)c1N]

The synthesis of Example 11 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.46 (d, J=8.4 Hz, 2H), 7.38 (t, J=8.0 Hz, 2H), 7.16 (t, J=7.2 Hz, 1H), 7.05-7.08 (m, 4H), 6.37-6.55 (m, 1H), 5.40-5.60 (brs, 2H), 5.12-5.30 (brs, 2H), 4.73-4.83 (m, 1H), 3.99-4.23 (m, 3H), 3.70-3.85 (m, 1H), 2.67-2.77 (m, 0.5H), 2.43-2.62 (m, 1.5H). m/z=462 [M+1]$^+$.

Example 12

(R,E)-5-amino-1-(1-(4-bromobut-2-enoyl)pyrrolidin-3-yl)-3-(4-phenoxyphenyl)-1H-pyrazole-4-carboxamide

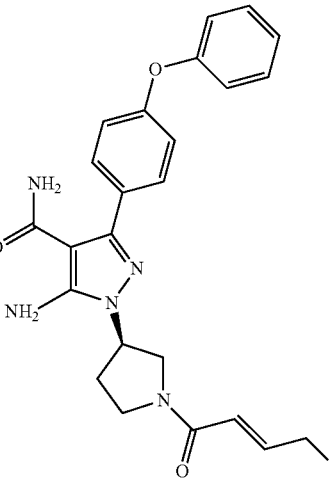

The synthesis of Example 12 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.48-7.50 (m, 2H), 7.35-7.39 (m, 2H), 7.14-7.18 (m, 1H), 7.69-7.09 (m, 5H), 6.34 (dd, J=10.8, 22.0 Hz, 1H), 5.2-5.6 (brs, 4H), 4.61-4.73 (m, 1H), 3.90-4.12 (m, 5H), 3.62-3.76 (m, 1H), 2.30-2.78 (m, 2H). m/z=510 [M+1]$^+$.

Example 13

(R,E)-4-(3-(5-amino-4-carbamoyl-3-(4-phenoxyphenyl)-1H-pyrazol-1-yl)pyrrolidin-1-yl)-4-oxobut-2-en-1-yl acetate

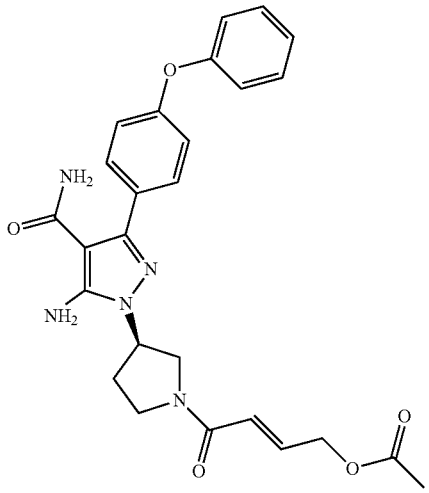 [SMILES: CC(=O)OC/C=C/C(=O)N1CC[C@@H](n2nc(-c3ccc(Oc4ccccc4)cc3)c(C(N)=O)c2N)C1]

The synthesis of Example 13 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.47-7.50 (m, 2H), 7.35-7.39 (m, 2H), 7.14-7.18 (m, 1H), 7.05-7.09 (m, 4H), 6.88-6.93 (m, 1H), 6.32 (dd, J=14.8, 22.8 Hz, 1H), 5.52 (s, 1H), 5.48 (s, 1H), 5.21 (brs, 2H), 4.61-4.75 (m, 3H), 3.93-4.07 (m, 3H), 3.61-3.76 (m, 1H), 2.30-2.80 (m, 2H), 2.10 (s, 3H). m/z=490 [M+1]$^+$.

Example 14

(R,E)-5-amino-1-(1-(4-(methylsulfonamido)but-2-enoyl)pyrrolidin-3-yl)-3-(4-phenoxyphenyl)-1H-pyrazole-4-carboxamide

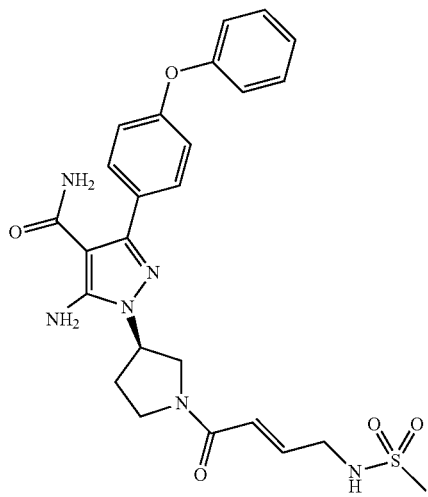 [SMILES: CS(=O)(=O)NC/C=C/C(=O)N1CC[C@@H](n2nc(-c3ccc(Oc4ccccc4)cc3)c(C(N)=O)c2N)C1]

The synthesis of Example 14 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.48-7.52 (m, 2H), 7.35-7.39 (m, 2H), 7.14-7.18 (m, 1H), 7.05-7.08 (m, 4H), 6.85-6.93 (m, 1H), 6.38 (dd, J=14.8, 21.2 Hz, 1H), 5.55 (s, 1H), 5.50 (s, 1H), 5.21 (brs, 2H), 4.60-4.74 (m, 2H), 3.92-4.07 (m, 5H), 3.61-3.78 (m, 1H), 2.98 & 2.97 (s, 3H), 2.30-2.86 (m, 2H). m/z=525 [M+1]$^+$.

Example 15

(R,E)-5-amino-1-(1-(4-hydroxybut-2-enoyl)pyrrolidin-3-yl)-3-(4-phenoxyphenyl)-1H-pyrazole-4-carboxamide

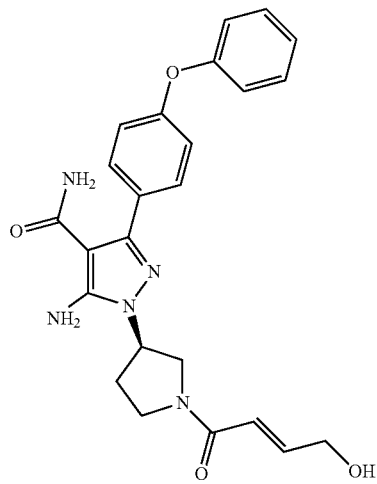 [SMILES: NC(=O)c1c(-c2ccc(Oc3ccccc3)cc2)nn([C@@H]2CCN(C(=O)/C=C/CO)C2)c1N]

The synthesis of Example 15 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.45-7.48 (m, 2H), 7.35 (t, J=8.0 Hz, 2H), 7.14 (t, J=7.6 Hz, 1H), 7.03-7.06 (m, 4H), 6.97-7.01 (m, 1H), 6.33-6.43 (m, 1H), 5.56 (s, 1H), 5.48 (s, 1H), 5.20-5.41 (brs, 2H), 4.62-4.72 (m, 1H), 4.33-4.36 (m, 2H), 3.89-4.11 (m, 3H), 3.60-3.74 (m, 1H), 2.67-2.77 (m, 0.5H), 2.49-2.62 (m, 0.5H), 2.26-2.44 (m, 1H). m/z=448 [M+1]$^+$.

Example 16

(R)-5-amino-1-(1-(but-2-ynoyl)pyrrolidin-3-yl)-3-(4-phenoxyphenyl)-1H-pyrazole-4-carboxamide

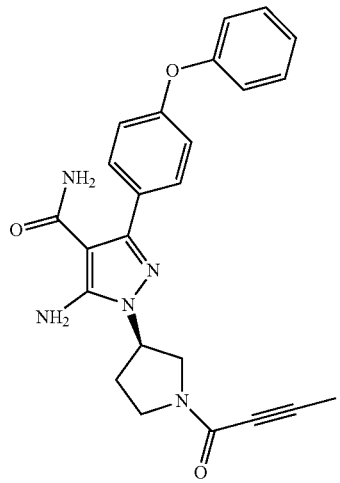 [SMILES: CC#CC(=O)N1CC[C@@H](n2nc(-c3ccc(Oc4ccccc4)cc3)c(C(N)=O)c2N)C1]

The synthesis of Example 16 was accomplished using a procedure analogous to that described in Example 1 with (R)-5-amino-3-(4-phenoxyphenyl)-1-(pyrrolidin-3-yl)-1H-pyrazole-4-carboxamide.

$^1$H NMR (400 MHz, CDCl$_3$) δ 7.48-7.51 (m, 2H), 7.35-7.39 (m, 2H), 7.14-7.17 (m, 1H), 7.05-7.08 (m, 4H), 5.65 (s, 1H), 5.62 (s, 1H), 5.30 (brs, 2H), 4.70-4.73 (m, 1H), 3.95-4.15 (m, 2H), 3.78-3.87 (m, 1.5H), 3.58-3.61 (m, 0.5H), 2.57-2.65 (m, 1H), 2.34-2.39 (m, 1H), 2.00 & 1.97 (s, 3H). m/z=430 [M+1]$^+$.

Example 17

(R)-5-amino-3-(4-phenoxyphenyl)-1-(1-propioloylpyrrolidin-3-yl)-1H-pyrazole-4-carboxamide

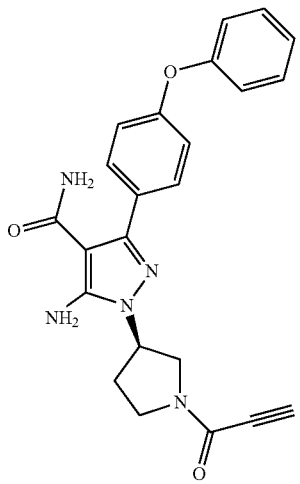 [SMILES: C#CC(=O)N1CC[C@@H](n2nc(-c3ccc(Oc4ccccc4)cc3)c(C(N)=O)c2N)C1]

The synthesis of Example 17 was accomplished by condensation of propiolic acid and (R)-5-amino-3-(4-phenoxyphenyl)-1-(pyrrolidin-3-yl)-1H-pyrazole-4-carboxamide in DMF in the presence of HOBt and EDCI.

$^1$H NMR (400 MHz, CDCl$_3$) δ 7.48-7.50 (m, 2H), 7.35-7.39 (m, 2H), 7.14-7.17 (m, 1H), 7.05-7.08 (m, 4H), 5.63 (s, 1H), 5.61 (s, 1H), 5.30 (brs, 2H), 4.72-4.75 (m, 1H), 3.82-4.14 (m, 3.5H), 3.61-3.64 (m, 0.5H), 3.08 & 3.04 (s, 1H), 2.58-2.66 (m, 1H), 2.35-2.41 (m, 1H). m/z=416 [M+1]$^+$.

Example 18

5-amino-1-((1s,4s)-4-(but-2-ynamido)cyclohexyl)-3-(4-phenoxyphenyl)-1H-pyrazole-4-carboxamide

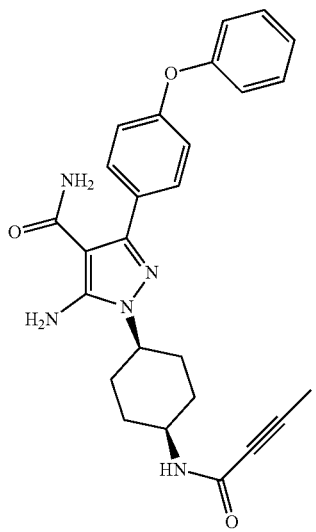 [SMILES: CC#CC(=O)N[C@H]1CC[C@@H](n2nc(-c3ccc(Oc4ccccc4)cc3)c(C(N)=O)c2N)CC1]

The synthesis of Example 18 was accomplished using a procedure analogous to that described in Example 1.

$^1$H NMR (400 MHz, CDCl$_3$) δ 7.50-7.52 (m, 2H), 7.36-7.40 (m, 2H), 7.14-7.18 (m, 1H), 7.04-7.10 (m, 4H), 6.09 (d, J=8.0 Hz, 1H), 5.44 (s, 2H), 5.22 (brs, 2H), 4.22-4.25 (m, 1H), 3.86-3.88 (m, 1H), 1.61-2.13 (m, 8H), 1.94 (s, 3H). m/z=458 [M+1]$^+$.

Assays on Biological Activities
Biological Activities of the Compounds
In Vitro Inhibitory Activities on BTK (Determination of IC$_{50}$ values)

The half inhibition concentrations (IC$_{50}$ values) of the compounds disclosed herein on Btk were determined at both enzymatic level and cellular level: the ability of the compounds to inhibit the activity of Btk kinase was determined in an enzymtic activity assay, and the inhibitory effect of the compounds on BCR-induced calcium flux in cells was determined in a cellular function assay.

A platform for determining the Btk kinase activity was established using a Homogeneous Time-Resolved Fluorescence (HTRF) methodology, and the activities of the compounds were determined. The compounds were gradiently diluted 3 folds starting from 1 mM with 100% DMSO (totally 11 concentrations). 4 μL of each sample with a different concentration was added into 96 μL of reaction buffer (50 mM HEPES, pH 7.4, 10 mM MgCl$_2$, 1 mM EGTA, 0.01% Tween-20, 0.005% BAS, 2 mM DTT). 2.5 μL of each solution was added to a 384-well plate (OptiPlate-384, PerkinElmer), followed by adding 5 μL of Btk kinase (Millipore). The mixture was centrifuged to mix well, followed by adding 2.5 μL of a mixture of ATP (final concentration designated as K$_m$) and TK petide (HTRF® KinEASE™-TK, Cisbio) to initiate the reaction (total reaction volume being 10 μL). The 384-well plate was put in an incubator and the reaction was conducted at 23° C. for 120 min, followed by adding 5 μL of Eu3+ cryptate-labeled anti-phosphotyrosine antibody (Cisbio) and 5 μL of Streptavidin-XL-665 (HTRF® KinEASE™-TK, Cisbio) to terminate the reaction. After incubating in the incubator for 1 hour, the fluorescent value was read on Envision (PerkinElmer) (excited at 320 nm, and the emitted light was detected at 665 nm and 615 nm, the ratio therebetween being the enzymatic activity). The enzyme activity for each compound was determined at 11 concentrations, and $IC_{50}$ values were obtained by GraFit Software 6.0 (Erithacus Software).

The ability of the compounds to inhibit the release of calcium from intracellular calcium reservoir was determined by calcium flux using Fluo-4 Direct™ Calcium Assay Kits (Invitrogen) operated on FlexStation III (Molecular Devices) according to manufacturer's instructions. The specific procedures were as follows. Romas cells were cultured in RPMI-1640 (Invitrogen) supplemented with 10% FBS (Hyclone), centrifuged and washed, and re-plated in low serum medium in a 96-well plate ($1 \times 10^5$ cells per 45 μL per well), followed by adding 45 μL of fluorescent dye (Invitrogen) and incubating at 37° C. for 1 hour. Compounds to be assayed were gradiently diluted 3 folds with DMSO and then diluted 100 folds with low serum medium. 10 μL of each sample was added to a 96-well plate (Corning) containing cells (final concentration of DMSO was 0.01%). The 96-well plate (Corning) was incubated in an incubator (37° C., 5% $CO_2$) for 30 min. The compound-treated cells were stimulated with a goat anti-human IgM antibody (10 μg/ml; SouthernBiotech) and the fluorescent value was read in FlexStation III (excited at 494 nM and detected at 516 nM for 90 seconds). The data for each compound were fitted using GraphPad Prism 5 (GraphPad Software) and calculated to give corresponding $IC_{50}$ values.

Biological Data for Selected Compounds

Compounds prepared as described above were assayed according to the biological procedures described herein. The results are given in Table 1 below:

TABLE 1

| Compound No. | Structure | Btk $IC_{50}$ (nM) | Itk $IC_{50}$ (nM) |
|---|---|---|---|
| 1 | 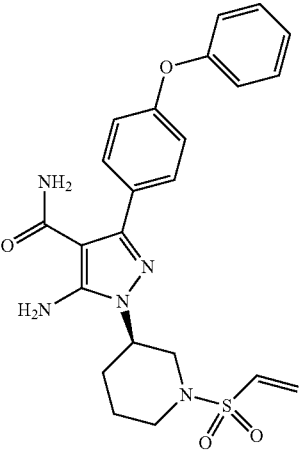 [SMILES: C=CS(=O)(=O)N1CCC[C@@H](n2nc(-c3ccc(Oc4ccccc4)cc3)c(C(N)=O)c2N)C1] | <100 | <100 |
| 2 | 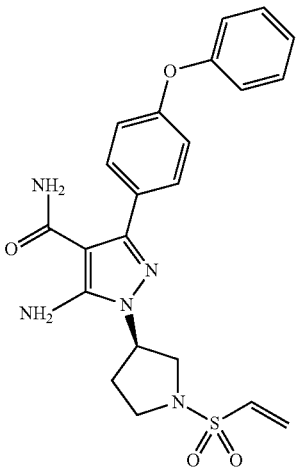 [SMILES: C=CS(=O)(=O)N1CC[C@@H](n2nc(-c3ccc(Oc4ccccc4)cc3)c(C(N)=O)c2N)C1] | <100 | <100 |

TABLE 1-continued
IC$_{50}$ of the compounds of the present invention
| Compound No. | Structure | Btk IC$_{50}$ (nM) | Itk IC$_{50}$ (nM) |
|---|---|---|---|
| 3 | 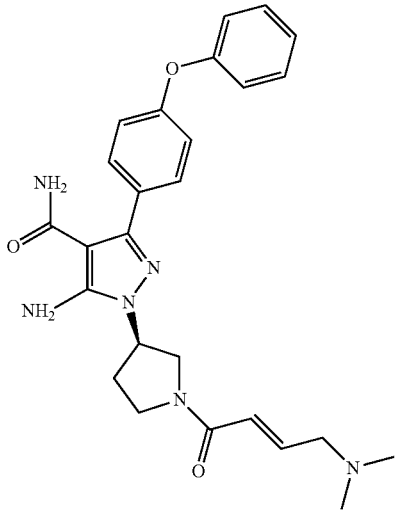 [SMILES: CN(C)C/C=C/C(=O)N1CC[C@@H](n2nc(-c3ccc(Oc4ccccc4)cc3)c(C(N)=O)c2N)C1] | <100 | >1000 |
| 4 | 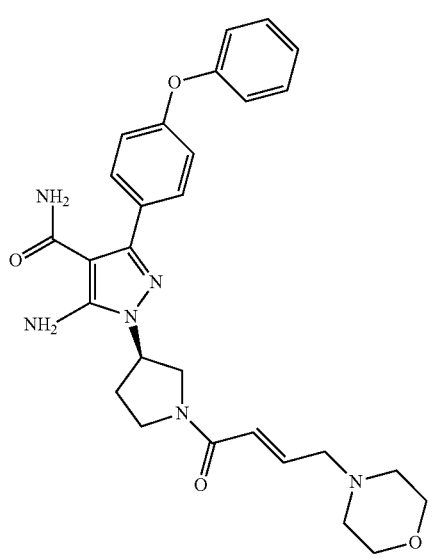 [SMILES: NC(=O)c1c(-c2ccc(Oc3ccccc3)cc2)nn([C@@H]2CCN(C(=O)/C=C/CN3CCOCC3)C2)c1N] | <100 | >1000 |

TABLE 1-continued

IC$_{50}$ of the compounds of the present invention

| Compound No. | Structure | Btk IC$_{50}$ (nM) | Itk IC$_{50}$ (nM) |
|---|---|---|---|
| 5 | 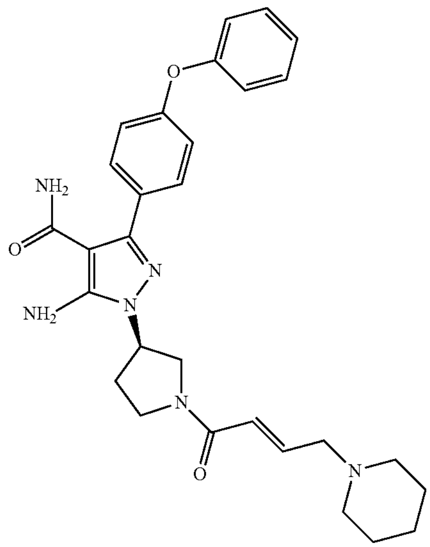 [SMILES: NC(=O)c1c(-c2ccc(Oc3ccccc3)cc2)nn([C@@H]2CCN(C(=O)/C=C/CN3CCCCC3)C2)c1N] | <100 | >1000 |
| 6 | 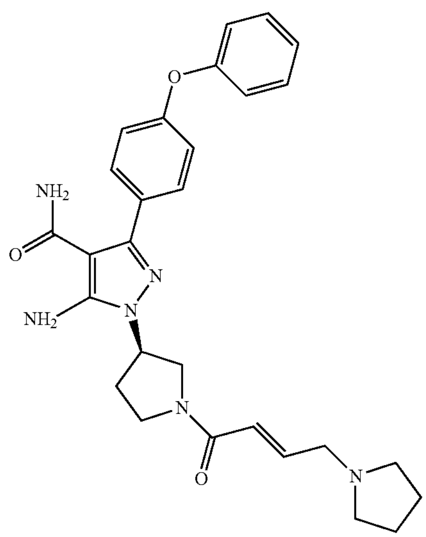 [SMILES: NC(=O)c1c(-c2ccc(Oc3ccccc3)cc2)nn([C@@H]2CCN(C(=O)/C=C/CN3CCCC3)C2)c1N] | <100 | >1000 |
| 7 | 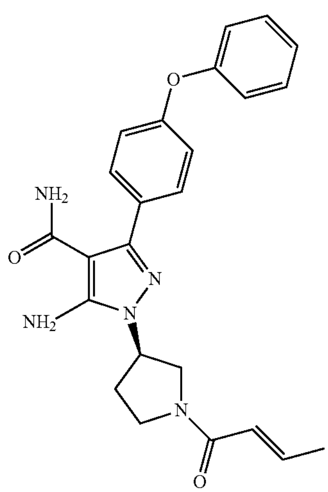 [SMILES: C/C=C/C(=O)N1CC[C@@H](n2nc(-c3ccc(Oc4ccccc4)cc3)c(C(N)=O)c2N)C1] | <100 | >1000 |

TABLE 1-continued

IC₅₀ of the compounds of the present invention

| Compound No. | Structure | Btk IC$_{50}$ (nM) | Itk IC$_{50}$ (nM) |
| --- | --- | --- | --- |
| 8 | 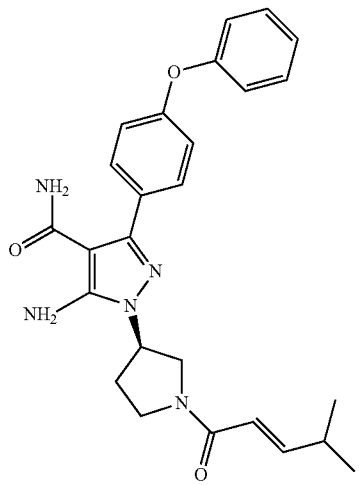 [SMILES: CC(C)/C=C/C(=O)N1CC[C@@H](n2nc(-c3ccc(Oc4ccccc4)cc3)c(C(N)=O)c2N)C1] | <100 | >1000 |
| 9 | 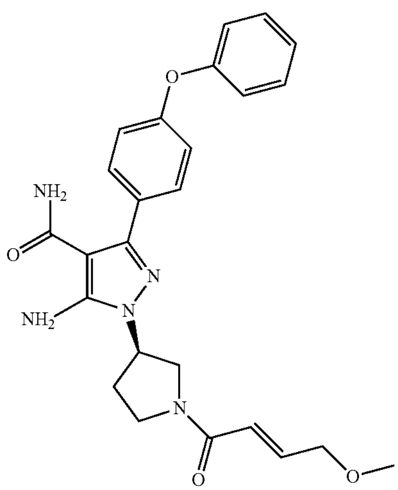 [SMILES: COC/C=C/C(=O)N1CC[C@@H](n2nc(-c3ccc(Oc4ccccc4)cc3)c(C(N)=O)c2N)C1] | <100 | >1000 |
| 10 | 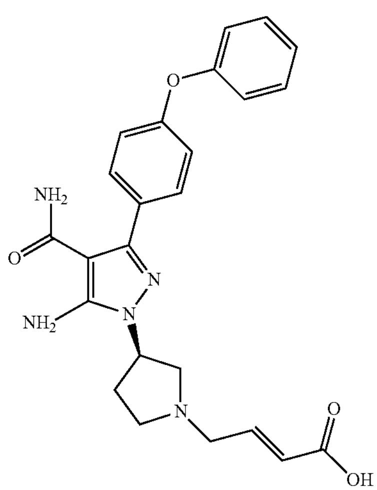 [SMILES: NC(=O)c1c(-c2ccc(Oc3ccccc3)cc2)nn([C@@H]2CCN(C/C=C/C(=O)O)C2)c1N] | <100 | >1000 |

TABLE 1-continued
| Compound No. | Structure | Btk IC$_{50}$ (nM) | Itk IC$_{50}$ (nM) |
|---|---|---|---|
| 11 | 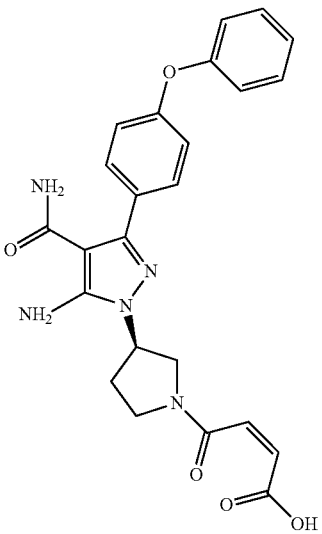 [SMILES: NC(=O)c1c(-c2ccc(Oc3ccccc3)cc2)nn([C@@H]2CCN(C(=O)/C=C\C(=O)O)C2)c1N] | <100 | >1000 |
| 12 | 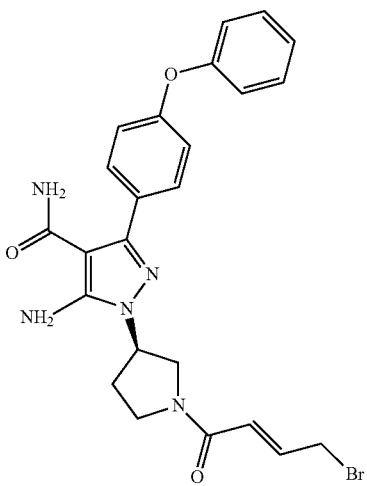 [SMILES: NC(=O)c1c(-c2ccc(Oc3ccccc3)cc2)nn([C@@H]2CCN(C(=O)/C=C/CBr)C2)c1N] | <100 | >1000 |
| 13 | 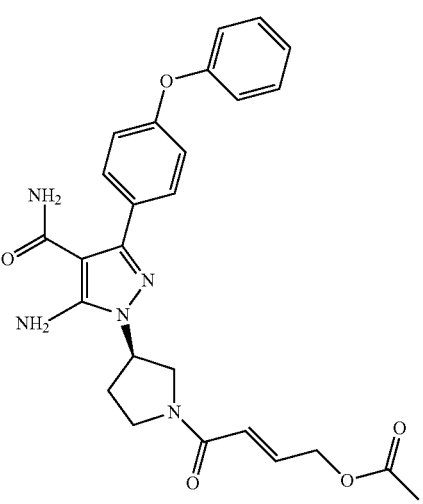 [SMILES: CC(=O)OC/C=C/C(=O)N1CC[C@@H](n2nc(-c3ccc(Oc4ccccc4)cc3)c(C(N)=O)c2N)C1] | <100 | >1000 |

TABLE 1-continued

IC$_{50}$ of the compounds of the present invention

| Compound No. | Structure | Btk IC$_{50}$ (nM) | Itk IC$_{50}$ (nM) |
|---|---|---|---|
| 14 | 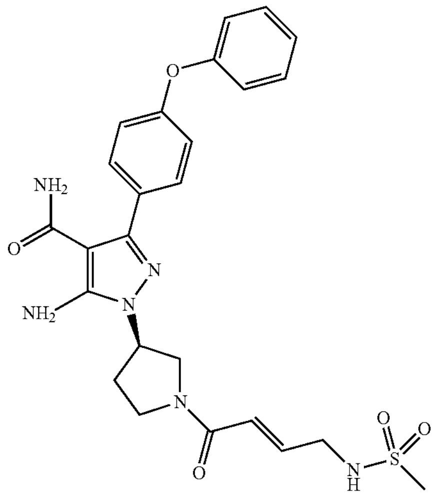 [SMILES: CS(=O)(=O)NC/C=C/C(=O)N1CC[C@@H](n2nc(-c3ccc(Oc4ccccc4)cc3)c(C(N)=O)c2N)C1] | <100 | >1000 |
| 15 | 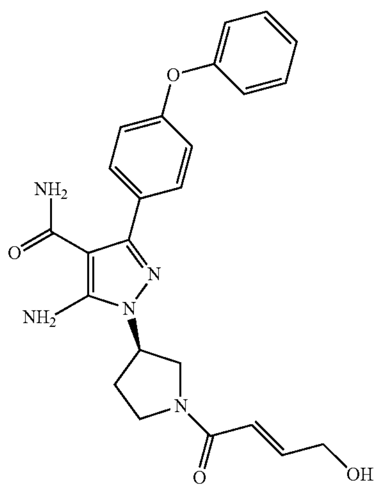 [SMILES: NC(=O)c1c(-c2ccc(Oc3ccccc3)cc2)nn([C@@H]2CCN(C(=O)/C=C/CO)C2)c1N] | <100 | >1000 |
| 16 | 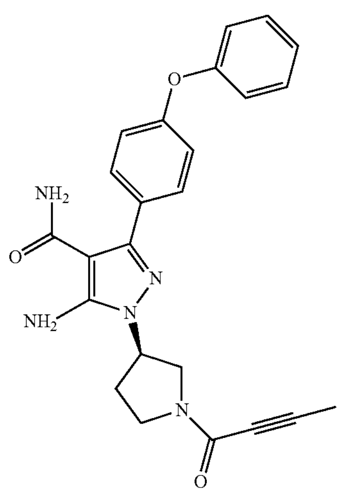 [SMILES: CC#CC(=O)N1CC[C@@H](n2nc(-c3ccc(Oc4ccccc4)cc3)c(C(N)=O)c2N)C1] | <100 | >1000 |

TABLE 1-continued

IC$_{50}$ of the compounds of the present invention

| Compound No. | Structure | Btk IC$_{50}$ (nM) | Itk IC$_{50}$ (nM) |
|---|---|---|---|
| 17 | 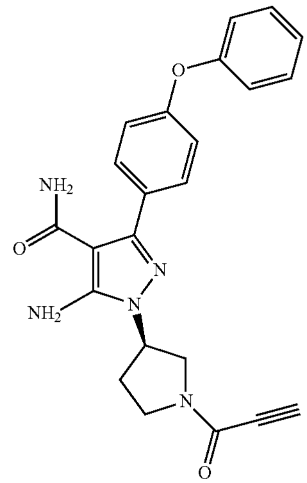 [SMILES: C#CC(=O)N1CC[C@@H](n2nc(-c3ccc(Oc4ccccc4)cc3)c(C(N)=O)c2N)C1] | <100 | <100 |
| 18 | 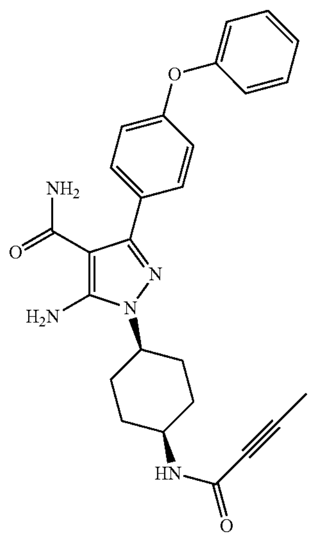 [SMILES: CC#CC(=O)N[C@H]1CC[C@@H](n2nc(-c3ccc(Oc4ccccc4)cc3)c(C(N)=O)c2N)CC1] | <100 | >1000 |

Determination of the Efficacy in Subcutaneously Xenografted Tumor Model in Mice

SPF grade female CB-17 SCID mice (4-5 week) were used. 0.1 ml of OCI-LY-10 cells suspended in serum-free medium (containing 5×106 cells, 30% Matrigel) were injected subcutaneously in both the left and the right flanks of mice. Mice were grouped and numbered when the average tumor volumes were more than 100 mm3, and the body weights and tumor volumes were determined. The mice were randomly grouped according to tumor volumes, and appropriate adjustments were made so that the average body weight in each group is on the same level. Animals were dosed orally on the same day when they were grouped, and body weights and tumor volumes were measured twice a week. Relative tumor growth (T/C) and Tumor growth inhibition (TGI) were the major test indeces.

The equation for calculating the tumor volume is V=0.5× a×b$^2$, wherein v is the tumor volume, a and b are the length and the width of the tumor, respectively. The relative tumor volume (RTV) was calculated according to the tumor volume with the equation RTV=V$_t$/V$_0$, wherein V$_0$ was the tumor volume at the time when the animals were grouped, and V$_t$ was the tumor volume at indicated time points. The equation for calculating the relative tumor proliferation rate was T/C (%)=T$_{RTV}$/C$_{RTV}$*100%. (T$_{RTV}$ was the RTV of treated group, and C$_{RTV}$ was the RTV of control group).

The equation for calculating the tumor growth inhibition rate was TGI (%)=(1−(tumor volume of the treated group−tumor volume of the treated group at the time when the animals were grouped)/(tumor volume of the control group−tumor volume of the control group at the time when the animals were grouped))*100%. The results were listed in Table 2.

TABLE 2

Tumor growth inhibition (TGI) of compounds of this invention

| Compounds | Dose (mg/kg) | Administration Method | Frequency | TGI (%) Day 3 | Day 8 | Day 11 |
|---|---|---|---|---|---|---|
| Example 7 | 100 | PO | QD | 33.27 | 19.00 | 11.28 |
| Example 9 | 100 | PO | QD | 45.79 | 39.37 | 43.05 |
| Example 16 | 100 | PO | QD | 14.97 | 19.53 | 29.98 |
| Example 16 | 50 | PO | BID | 35.97 | 32.25 | 44.47 |

Toxicity Test in Mice

20 Male CD-1 (ICR) mice (Beijing Vital River Laboratory Animal Technology Co., Ltd., approximately 5 weeks, 18-24 g) were divided into 4 groups with 5 mice in each group and orally administrated to the stomach with vehicle (20% Sulfobutyl Ether-β-Cyclodextrin), a suspension of the compound of example 9 (1000 mg/kg) or a suspension of the compound of example 16 (1000 mg/kg) once a day for 7 days. Body weights and conditions of mice were monitored every day, during which all mice were not fasting.

After continuous administration for 7 days, no health abnormalities were observed for all of the animals. Data of the average body weights of the mice are illustrated in Table 3, and the data show that body weights of all the animals increased and changed similarly. Table 4 shows the percent changes in mice body weight in the treated group over the control group, indicating that the groups administered with the compounds of example 9 and example 16 are similar to the control group (<2% difference), showing no toxicity.

TABLE 3

Average body weight of mice (g)

| | Day 1 | 2 | 3 | 4 | 5 | 6 | 7 |
|---|---|---|---|---|---|---|---|
| Vehicle | 24.6 | 24.8 | 25.2 | 25.6 | 26.1 | 26.7 | 26.9 |
| Example 9 | 24.4 | 24.6 | 25.1 | 25.6 | 26.4 | 26.9 | 27.2 |
| Example 16 | 24.8 | 25.3 | 25.7 | 25.9 | 26.3 | 26.5 | 26.9 |

TABLE 4

Changes (%) in mice body weight in treated group over control group

| | Day 1 | 2 | 3 | 4 | 5 | 6 | 7 |
|---|---|---|---|---|---|---|---|
| Example 9 | 100.0 | 100.0 | 100.3 | 101.1 | 101.8 | 101.7 | 101.7 |
| Example 16 | 100.0 | 101.1 | 100.8 | 100.6 | 99.8 | 98.5 | 98.9 |

Kinase Selectivity Test

In vitro activity in inhibiting ITK kinase was determined similar to that in respect of BTK kinase.

The inhibitory activity of the compound of Example 9 on BTK is very high with an IC50 value of 1.9 nM, comparable to the literature compound, Ibrutinib/PCI-32765, which has been approved for clinical application. The platform for the enzymatic assay on ITK kinase (another Tec Kinase, mainly expressed in T cells) was establish with the same method, and the inhibitory ability of the compound of example 9 on ITK was tested. The results showed that $IC_{50}$ value of this inhibition of ITK was more than 1000 nM. The selectivity of the compound of example 9 on BTK vs ITK was calculated as more than 1000 folds, while the selectivity of the literature compound, PCI-32765, was reported as approximately 100 folds. Accordingly, the selectivity of the compound of example 9 is significantly higher than that of PCI-32765. The specific results are displayed in Table 5 below.

TABLE 5

Inhibitory effects of the compound of Example 9 on BTK and ITK kinases

| Compounds | $IC_{50}$ (nM) BTK | ITK |
|---|---|---|
| PCI-32765 | 0.75 ± 0.06 | 75.3 ± 6.9 |
| Example 9 | 1.9 ± 0.18 | >1000 |

Efficacy Test in Arthritis Mice Models

Establishing Type II Collagen-Induced Arthritis Mice Model

Male DBA/1 mice of 6-8 weeks were accommodatively fed for one week before being subcutaneously injected with 0.1 mL of an emulsion of bovine type II collagen and Freunds' Complete Adjuvant (containing 100 μg of bovine type II collagen and 200 μg of inactivated mycobacterium tuberculosis) at tail vein. The mice were randomly grouped according to their arthritis scores when the onset of arthritis was observed after 4 weeks. Compounds were then administered continuously for 4 weeks, during which the arthritis scores were evaluated for each mouse and the body weights thereof were measure every other day. The criteria for evaluating the arthritis score were as follows:

0=normal;

1=erythema and mild swelling at ankle joint;

2=erythema and mild swelling from ankle joint to phalangeal joint or metacarpal joint;

3=erythema and moderate swelling from ankle joint to phalangeal joint or metacarpal joint;

4=erythema and severe swelling or ankylosis on whole foot including from ankle joint to phalangeal joint.

Each paw was scored according to the above criteria, and the highest score was 16.

The results are shown in FIG. 1. It was shown by the results that in the type II collagen-induced arthritis model, arthritis in the mice were significantly alleviated after administering the compound of example 9. Statistics showed that the degree of alleviating arthritis has an obvious dose dependency. The compound of example 9 showed good therapeutic effect on arthritis in the mice even under a very low dosage (0.3 mg/kg). It was found in a parallel comparison that the therapeutic effect of 0.3 mg/kg of the compound of example 9 was comparable to that of 3 mg/kg of PCI-32765, suggesting that the compound of example 9 has a wide therapeutic window.

What is claimed is:

1. A compound represented by Formula (III), or a pharmaceutically acceptable salt, solvate, metabolite, polymorph, ester, tautomer or prodrug thereof, formula (III)

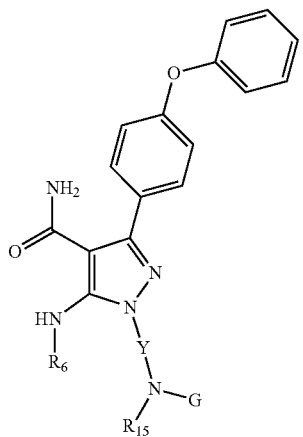

wherein:

Y and $R_{15}$ join to form a 5-membered heterocyclic ring;

G is selected from the group consisting of H,

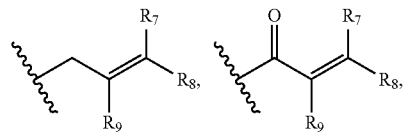

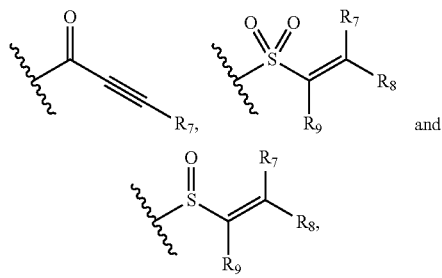

wherein $R_7$, $R_8$ and $R_9$ are each independently selected from the group consisting of H, halogen, —COOH, substituted or unsubstituted lower alkyl, and substituted or unsubstituted lower heteroalkyl;

$R_6$ is H; and n is 0, 1, 2, 3 or 4.

2. A compound according to claim 1, or a pharmaceutically acceptable salt, solvate, metabolite, polymorph, ester, tautomer or prodrug thereof, wherein

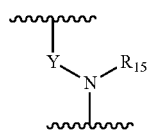

is selected from the group consisting of

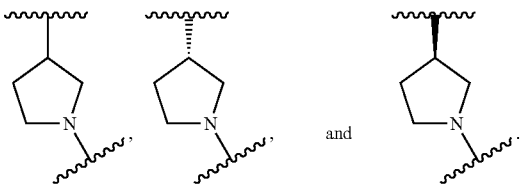 [SMILES: *C1CCN(*)C1 ; *[C@H]1CCN(*)C1 ; *[C@@H]1CCN(*)C1]

3. A compound according to claim 1, or a pharmaceutically acceptable salt, solvate, metabolite, polymorph, ester, tautomer or prodrug thereof, wherein G is selected from the group consisting of

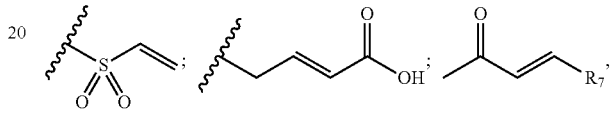

wherein $R_7$ is selected from the group consisting of H, —COOH and lower alkyl optionally substituted by the following groups: halogen, —OH, —O— lower alkyl, amino, monoalkylamino, dialkylamino, heterocycloalkylamino, alkylacyloxy and alkylsulfonamido; and

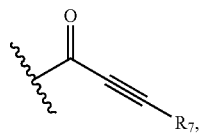

wherein $R_7$ is selected from the group consisting of H and lower alkyl.

4. A compound according to claim 1, or a pharmaceutically acceptable salt, solvate, metabolite, polymorph, ester, tautomer or prodrug thereof, wherein the compound is selected from:

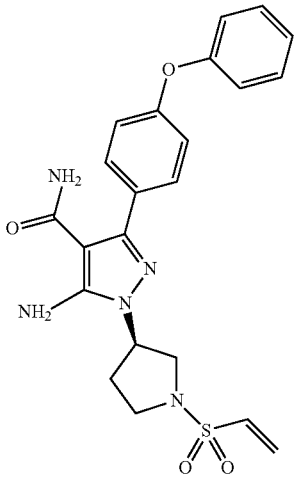

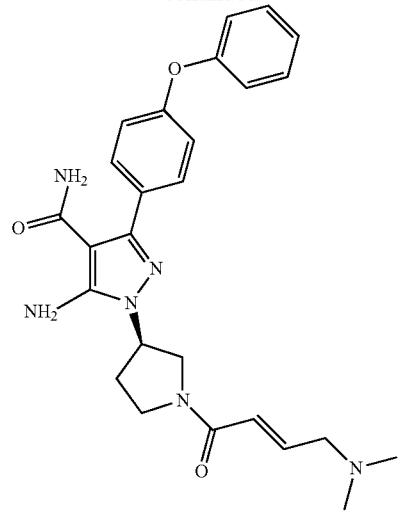
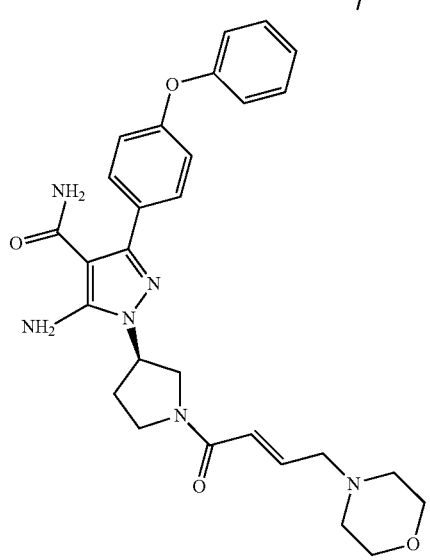
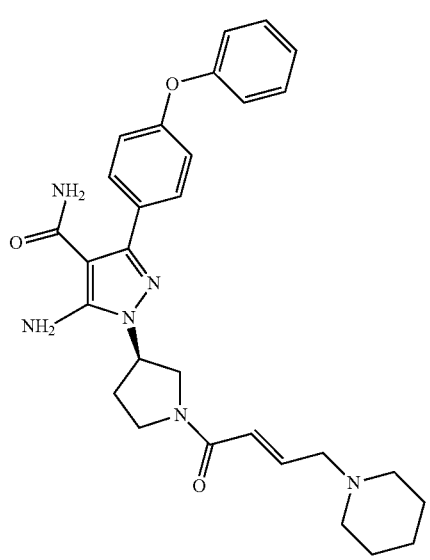
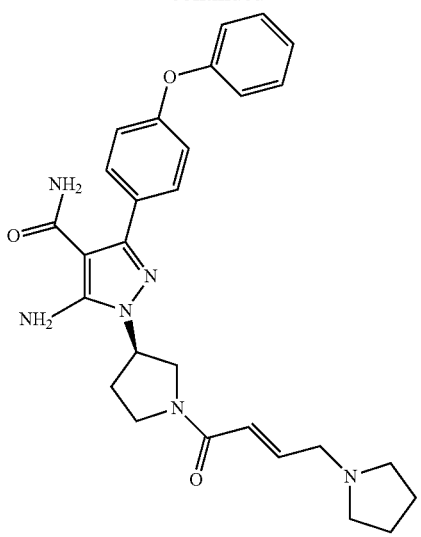
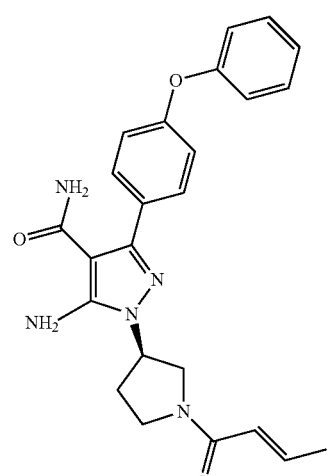
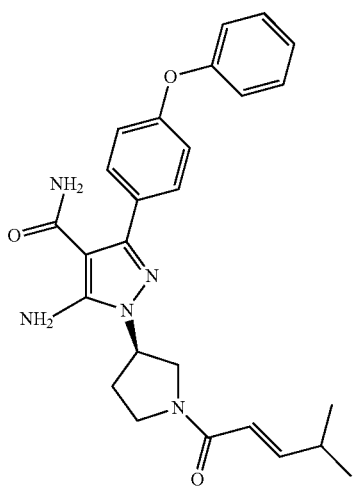

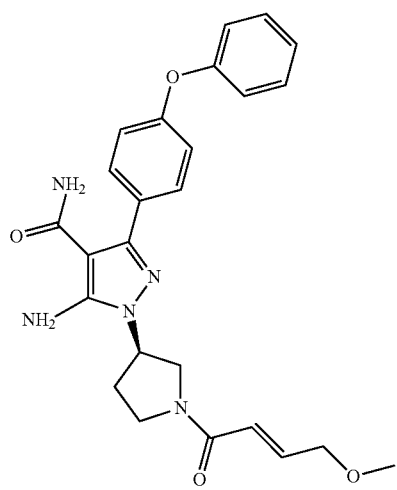
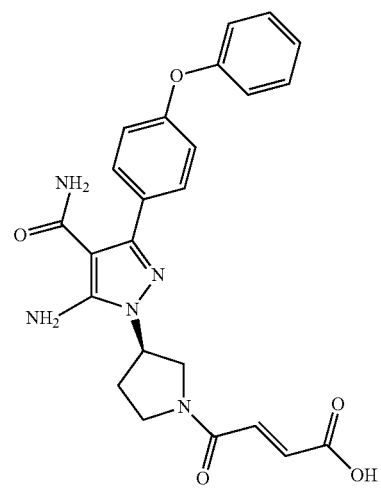
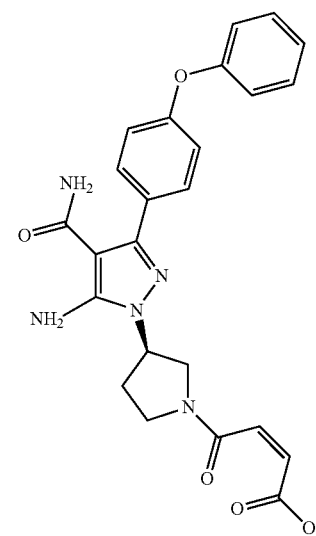
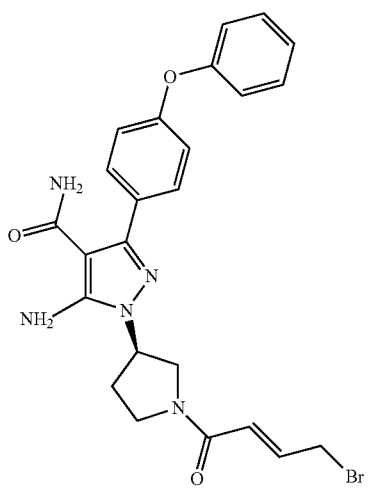
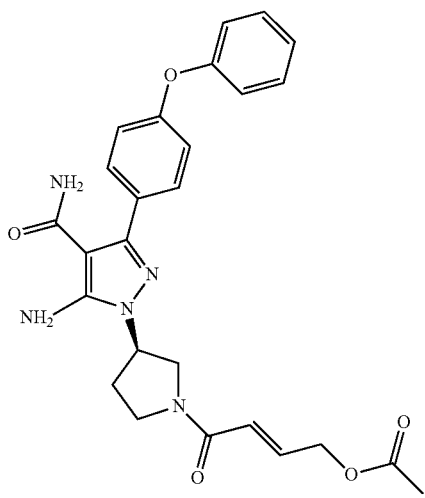
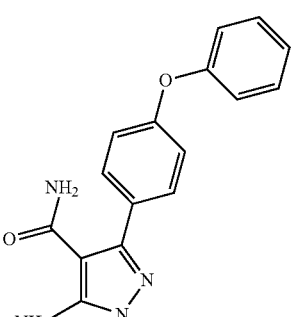
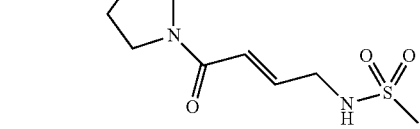

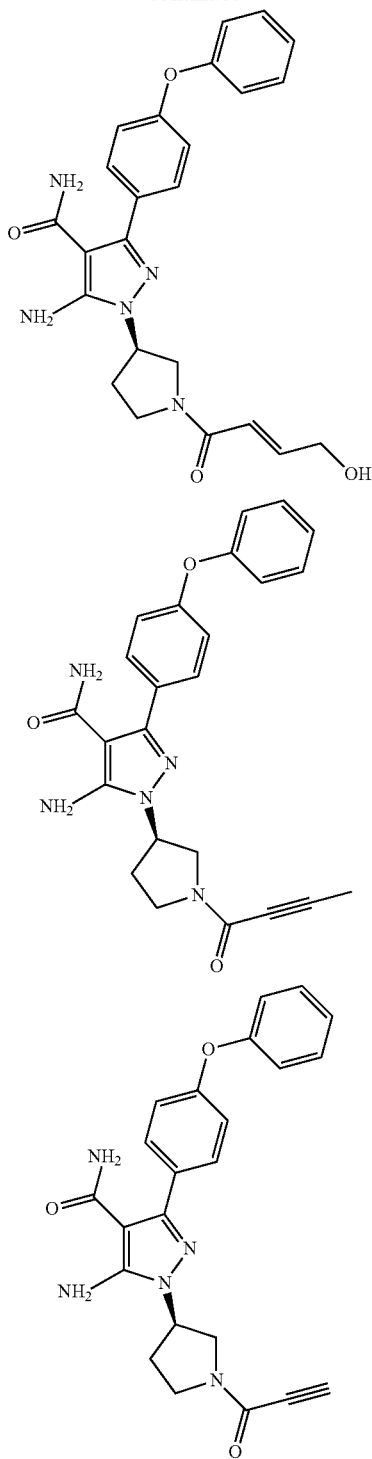

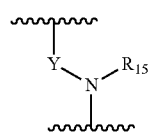

is

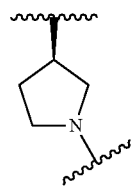

7. A compound according to claim 1, or a pharmaceutically acceptable salt, solvate, metabolite, polymorph, ester, tautomer or prodrug thereof, wherein G is selected from the group consisting of

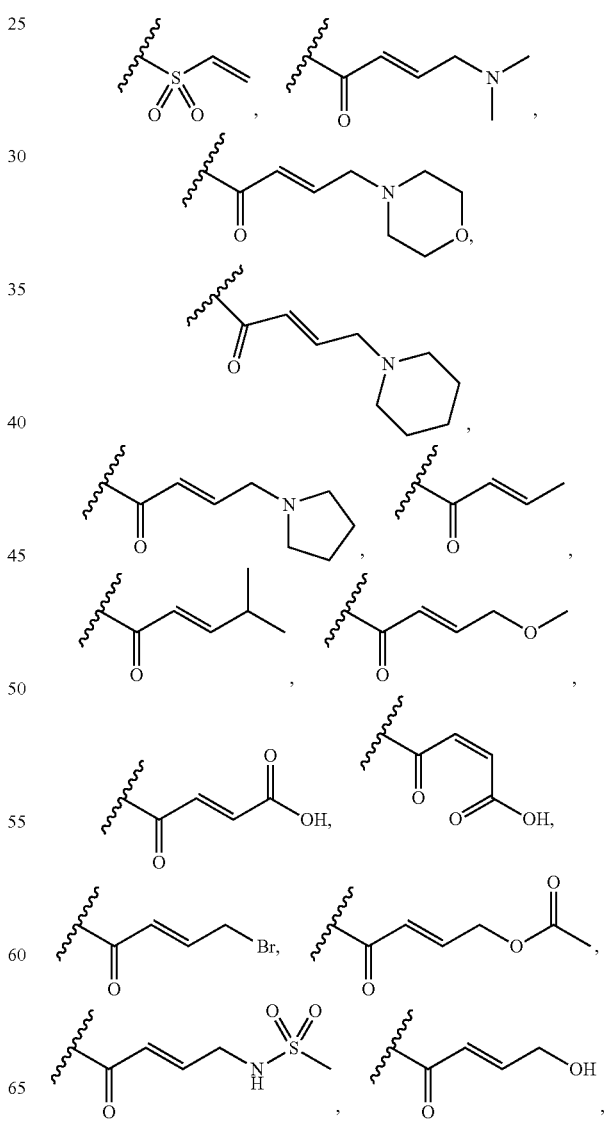

5. A pharmaceutical composition comprising therapeutically effective amount of the compound according to claim 1, or a pharmaceutically acceptable salt, solvate, metabolite, polymorph, ester, tautomer or prodrug thereof, and a pharmaceutically accepted carrier.

6. A compound according to claim 1, or a pharmaceutically acceptable salt, solvate, metabolite, polymorph, ester, tautomer or prodrug thereof, wherein -continued

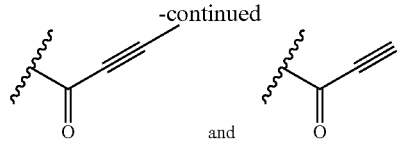

and .

8. A method for treating chronic lymphocytic lymphoma, diffuse large B cell lymphoma, follicular lymphoma or chronic lymphocytic leukemia comprising: administering to a mammal (especially a human being) in need thereof an therapeutically effective amount of a compound according to claim 1, or a pharmaceutically acceptable salt, solvate, metabolite, polymorph, ester, tautomer or prodrug thereof.

* * * * *